(12) United States Patent
Kowalczykowski et al.

(10) Patent No.: US 9,150,897 B2
(45) Date of Patent: Oct. 6, 2015

(54) EXPRESSION AND PURIFICATION OF FUSION PROTEIN WITH MULTIPLE MBP TAGS

(75) Inventors: Stephen Kowalczykowski, Davis, CA (US); Ryan Jensen, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/814,713

(22) PCT Filed: Aug. 5, 2011

(86) PCT No.: PCT/US2011/046846
§ 371 (c)(1),
(2), (4) Date: Apr. 15, 2013

(87) PCT Pub. No.: WO2012/019157
PCT Pub. Date: Feb. 9, 2012

(65) Prior Publication Data
US 2013/0203116 A1     Aug. 8, 2013

Related U.S. Application Data

(60) Provisional application No. 61/371,503, filed on Aug. 6, 2010.

(51) Int. Cl.
*C12P 21/06* (2006.01)
*C12N 1/20* (2006.01)
*C07K 1/00* (2006.01)
*C12P 21/00* (2006.01)
*C12N 15/62* (2006.01)

(52) U.S. Cl.
CPC ............... *C12P 21/00* (2013.01); *C12N 15/62* (2013.01); *C07K 2319/23* (2013.01); *C07K 2319/24* (2013.01)

(58) Field of Classification Search
CPC ........... C12N 9/00; C12N 1/20; C07K 14/435
USPC ................................ 435/69.1, 6; 530/350
See application file for complete search history.

(56) References Cited

U.S. PATENT DOCUMENTS

| 6,177,280 B1 * | 1/2001 | Yan et al. | 506/6 |
| 7,741,053 B2 * | 6/2010 | Mehigh et al. | 435/7.1 |
| 2006/0024786 A1 * | 2/2006 | Tomasevic et al. | 435/69.1 |

* cited by examiner

*Primary Examiner* — Maryam Monshipouri
(74) *Attorney, Agent, or Firm* — Kilpatrick Townsend & Stockton LLP

(57) ABSTRACT

The present invention provides a new method for recombinantly expressing a protein of interest, such as the human BRCA2 protein, BLM protein, CtIP protein, or EXOI protein, by expressing the protein in the form of a fusion protein comprising two maltose-binding protein (MBP) or glutathione-S-transferase (GST) tags. The expression cassette useful for this method and the fusion protein produced by this method are also described.

19 Claims, 23 Drawing Sheets

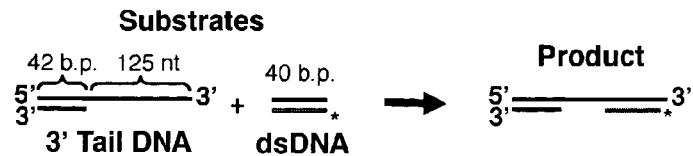
Figure 3A
Figure 3B
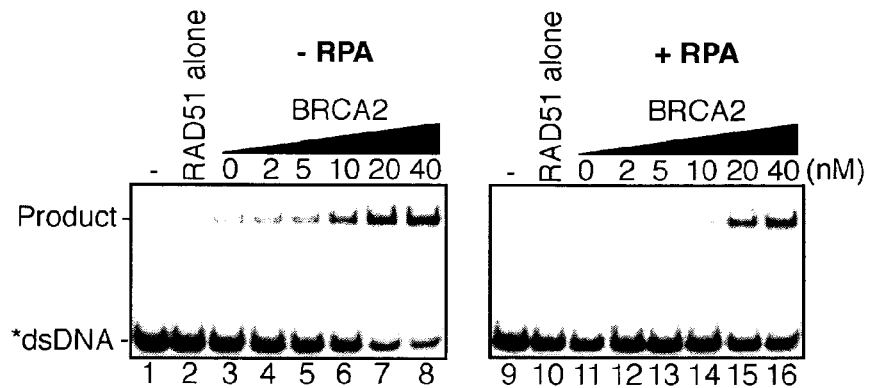
Figure 3C

3' Tail DNA
+
-/+ BRCA2
+
RAD51
↓ 5'
*dsDNA
30'

Transfect 293T cells

Harvest cell lysates
31 hrs post-transfection

Amylose

HiTrap Q

3' Tail DNA
+
RPA
↓ 5'
-/+ BRCA2
+
RAD51
↓ 5'
*dsDNA
1', 5', 15', 30', 60'
Figure 13A
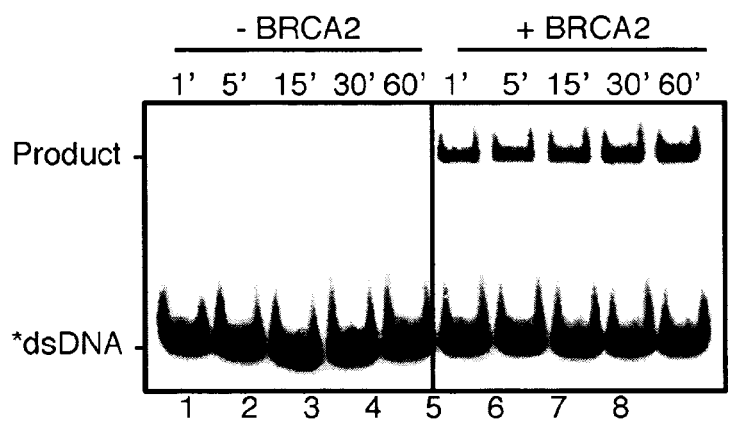
Figure 13B
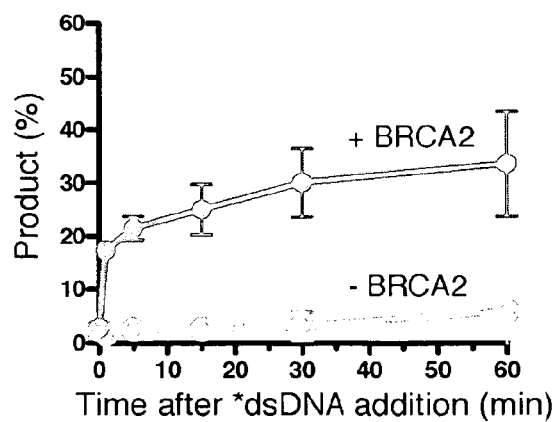
Figure 13C

EXPRESSION AND PURIFICATION OF FUSION PROTEIN WITH MULTIPLE MBP TAGS

RELATED APPLICATIONS

The present application is a U.S. National Phase of PCT/US2011/046846, filed Aug. 5, 2011, which claims priority to U.S. Provisional Patent Application Ser. No. 61/371,503, filed Aug. 6, 2010, the contents of which are hereby incorporated by reference in their entirety for all purposes.

STATEMENT AS TO RIGHTS TO INVENTIONS MADE UNDER FEDERALLY SPONSORED RESEARCH AND DEVELOPMENT

This invention was made with Government support under Grant No. GM062653, awarded by the National Institutes of Health and ARMY/MRCM Grant No. W81XWH-09-1-0098. The Government has certain rights in this invention.

BACKGROUND OF THE INVENTION

Recombinant DNA technologies have offered a unique opportunity for scientists to produce essentially unlimited quantity of proteins of interest for therapeutic use and also for further research. Some difficulties however can seriously hinder the recombinant production of certain proteins, such as proteins of larger sizes and/or of limited solubility. For example, the BRCA2 protein has been the focus of intense research due to the involvement of this protein in various human epithelial cancers including breast and ovarian cancers, but efforts to recombinantly producing this protein has been largely unsuccessful. The present inventors devised a new strategy in the recombinant production of proteins and this new strategy has demonstrated unexpected effectiveness in improving the quantity of expression, solubility of the recombinant protein, and ease of purification of the protein. Their discovery is therefore a significant improvement, especially for certain proteins, such as the BRCA2 protein, which have the characteristics of relatively large size and low solubility, and which other researchers have previously been unable to recombinantly produce in desirable quantity and quality.

BRIEF SUMMARY OF THE INVENTION

This invention provides new methods and expression cassettes useful for the recombinant expression of a protein of interest, especially those that may be difficult to produce in their full length and/or in large quantity by the conventional methods. According to the methods of this invention, the protein of interest is produced in the form of a fusion protein in which the protein is fused with two or more tags that provide a binding moiety for affinity-based purification as well as render the fusion protein a higher solubility than that of the original protein. Such tags include the maltose-binding protein (MBP) tag and the glutathione-S-transferase (GST) tag. In each fusion protein a multiplicity of the same tags are used, for example, two or more MBP tags are present in one fusion protein, whereas another fusion protein may include two or more GST tags. Each of the MBP or GST tags is located at the N- or C-terminus of the protein, and in some cases all of the MBP or GST tags are located at the same N- or C-terminus, whereas in other cases there may be one or more MBP or GST tags at each terminus. Thus, in one aspect, the present invention relates to a method for recombinant expression of a protein. The method includes these steps: (1) introducing an expression cassette into a host cell, wherein the expression cassette comprises a polynucleotide sequence encoding a protein of interest and at least two additional coding sequences, wherein the at least two additional coding sequence encode maltose binding protein (MBP) tags, or wherein the at least two additional coding sequences encode glutathione-S-transferase (GST) tags, such that the expression cassette encodes a fusion protein comprising the protein of interest and at least two MBP or GST tags located at the N-terminus and/or C-terminus of the protein of interest; and (2) maintain the cell under conditions permissible for the expression of the fusion protein, whereby producing the fusion protein. In some cases, the method may further include a purification step following step (2), wherein the fusion protein is purified from the environment in which it is recombinantly expressed. In other cases, the method may further include a step of cleaving off the tags by the action of protease, when a protease cleavage site is engineered during the construction of the expression cassette between the protein of interest and the tags.

In some embodiments, the fusion protein consists essentially of the protein of interest (such as a human BRCA2 protein, BLM protein, CtIP protein, or EXOI protein) and the two MBP tags or two GST tags. The two MBP or GST tags are both located at the N-terminus of the protein of interest in some cases, whereas in other cases one MBP or GST tag is located at the N-terminus of the protein of interest and the other MBP or GST tag is located at the C-terminus of the protein of interest. In some embodiments, the protein of interest is a BRCA2 protein, especially a human BRCA2 protein. In other embodiments, the protein of interest is a human BLM protein, CtIP protein, or EXOI protein. In some embodiments, the fusion protein has at least two MBP or GST tags at the N-terminus, with the option of having additional MBP or GST tag or tags at the N-terminus and/or C-terminus. In some embodiments, the expression cassette comprises a cytomegalovirus (CMV) promoter. In other embodiments, the cell used for expressing the fusion protein is a prokaryotic cell or a eukaryotic cell, such as a human cell, especially a stable cell line, e.g., the HEK-293T cell.

In another aspect, the present invention relates to a fusion protein produced by the methods described above. In some embodiments, the protein of interest is a BRCA2 protein, such as a human BRCA2 protein. In other embodiments, the protein of interest is a human BLM protein, CtIP protein, or EXOI protein. In some embodiments, the fusion protein comprises two MBP or GST tags at the N-terminus, with the possibility that additional MBP or GST tag or tags may be present at the N-terminus and/or C-terminus. For example, such a fusion protein may comprise a human BRCA2 protein and two MBP or GST tags at the N-terminus; or the fusion protein may consists essentially of a human BRCA2 protein and two MBP or GST tags at the N-terminus. Optionally, a proteolytic cleavage site is placed between the protein of interest and the tags so that the tags may be readily removed by the use of an appropriate protease.

In a further aspect, the present invention relates to an expression cassette that encodes for the fusion protein of this invention. In other words, the expression cassette comprising two polynucleotide sequences, each encoding an MBP or GST tag, prior to the coding sequence for a protein of interest is ligated into the cassette. In some cases, a CMV promoter is used in the expression cassette in an operably linked position to the coding sequences for the protein of interest and the MBP or GST tags. In other cases, a protease cleavage site is inserted between the tags and the protein of interest to facilitate the removal of the tags, if desired. A host cell containing the expression cassette is also provided. The host cell may be a prokaryotic or eukaryotic cell, such as human cell, especially an established stable cell line, e.g., HEK-293T cell.

In yet another aspect, the present invention relates to an screen assay for identifying inhibitors or stimulators of protein interaction between the BRCA2 protein and the RAD51 protein. Such inhibitors or stimulators can be useful therapeutics in the treatment of cancer. The screening method includes these steps: (1) contacting a candidate compound with a RAD51 protein and the BRAC2 protein produced by the method of this invention (such as a fusion between the wild-type full length human BRCA2 protein and 2 MBP tags at its N-terminus) under conditions permissible of binding between the RAD51 protein and the BRCA2 protein; and (2) comparing the level of binding between the RAD51 protein and the BRCA2 protein with or without the candidate compound. If the BRCA2-RAD51 association decreases or increases in the presence of a candidate compound, then this compound is indicated as an inhibitor or stimulator of the BRCA2-RAD51 binding, respectively.

BRIEF DESCRIPTION OF THE DRAWINGS

FIG. 13. Kinetic analysis of RAD51-mediated DNA strand exchange stimulated by BRCA2. (A) In this reaction scheme, a time course from 1-60 minutes was performed after the addition of the labeled dsDNA. Concentrations of DNA and proteins were as in FIG. 5A. (B) Autoradiogram of the gel from reactions following the time course as described in (A) with 40 nM BRCA2 (+BRCA2) or without BRCA2 (−BRCA2). (C) Quantification of the gel in (B). Error bars represent the S.D.

DEFINITIONS

Figure 1A:
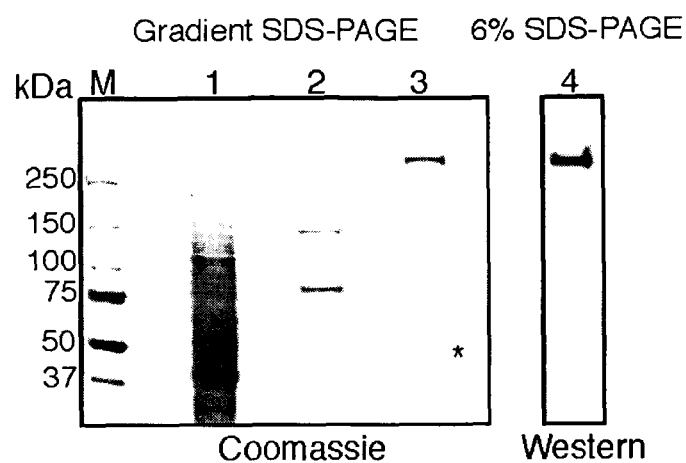
FIG. 1. Protein interactions with purified full-length human BRCA2. (A) Left: Gradient (4-15%) SDS-polyacrylamide gel stained with Coomassie blue showing total cell lysate from 293T cells transfected with 2XMBP-tagged full length BRCA2 (lane 1), amylose purified BRCA2 (lane 2), and BRCA2 after HiTrap Q purification (lane 3; 3 µg). M, molecular mass standards. 2XMBP-BRCA2 has a predicted molecular mass of 470 kDa. The asterisk denotes the β-tubulin contaminant in the protein preparation. Right: 6% SDS-polyacrylamide gel showing a western blot of the final purified protein (lane 4, 10 ng) using an antibody to the C-terminus (a.a. 3245-3418, Ab-2). (B) Mitomycin C clonogenic survival assay showing complementation of brca2$^{-/-}$ (VC8) mutant cells stably expressing either single MBP-tagged BRCA2 (✷) or the dual 2XMBP-tagged BRCA2 (✶). The parental cells, wild type V79 (■) and brca2 mutant VC8 (✧) are shown for comparison. The graph shows the mean survival for three independent experiments. Errors bars represent standard deviation (S.D.). (C) Protein Pull-downs. 2XMBP-BRCA2 (2 µg) was incubated with 1 µg of SSB (lane 6), RecA (lane 7), yRad51 (lane 8), or hRAD51 (lane 9) for 30 minutes at 37° C. The protein complexes were then captured on amylose beads, washed, eluted, analyzed by gradient PAGE, and stained with SyproOrange. Lanes 1-4 show the candidate protein input and lanes 10-13 contain proteins incubated with amylose beads in the absence of BRCA2. The asterisk denotes the β-tubulin contaminant. (D) Protein Pull-downs. 2XMBP-BRCA2 (2 µg) was incubated with 1 µg of hDMC1 (lane 5), hRPA (lane 6), or hRAD52 (lane 7). The protein complexes were processed as in (C). (E) 2XMBP-BRCA2 (2 µg) was incubated with increasing amounts of purified RAD51 (0.25-6 µg) for 30 minutes at 37° C. Lanes 1-4 contain increasing amounts of RAD51 (0.1-0.8 µg) to generate a standard curve. In lanes 5-11, the protein complexes were processed as described in (C). Lane 5 contains 2XMBP-BRCA2 in the absence of RAD51. Lanes 6-10 show increasing concentrations of RAD51 incubated with 2XMBP-BRCA2. Lane 11 is a control showing the maximal amount of RAD51 (6 µg) used in the pull-down experiments in the absence of 2XMBP-BRCA2. Lanes 12-14 contain increasing concentrations of 2XMBP-BRCA2 (0.1-2 µg) to generate a standard curve for BRCA2. (F) The data from (E) were fit to a segmental linear regression (Prism 5.0b), and reveal that BRCA2 has both high affinity binding sites for RAD51, and low affinity binding sites. Error bars represent S.D. for two independent experiments.

The term "BRCA2 protein (breast cancer type 2 susceptibility protein)," as used herein, refers to any naturally occurring variants or mutants, interspecies homologs/orthologs, and man-made variants of human BRCA2 protein. The human BRCA2 gene is located on the long (q) arm of chromosome 13 at position 12.3 (13q12.3), from base pair 31,787,616 to base pair 31,871,804. The cDNA sequence of a human wild-type BRCA2 gene is set forth in GenBank Accession No. NM_000059.3 and the amino acid sequence of the human wild-type BRCA2 protein is set forth in GenBank Accession No. NP_000050.2. A BRCA2 protein within the meaning of this application typically has at least 80%, or 90%, or 95% sequence identity to the human wild-type BRCA2 protein. The human EXOI or exonuclease I protein is encoded by cDNA sequence set forth in GenBank Accession No. BC007491.2. The human BLM protein or Bloom's syndrome protein is encoded by cDNA sequence set forth in GenBank Accession No. BC093622.1. The human CtIP or retinoblastoma binding protein 8 (RBBP8) protein is encoded by cDNA sequence set forth in GenBank Accession No. BC030590.1. Similar to the useage of the term "BRCA2 protein," the EXOI, BLM, or CtIP protein encompasses any naturally occurring variants or mutants, interspecies homologs or orthologs, and man-made variants of each corresponding wild-type human protein.

A "maltose binding protein tag" or "MBP tag" is derived from an *Escherichia coli* protein involved in the maltose/maltodextrin system. An MBP tag may be the full length, a portion, or a modified version of the wild-type *E. coli* maltose binding protein, so long as the presence of the MBP tag increases the solubility of the resulting recombinant fusion protein and confers to the fusion protein the binding affinity to amylose. An exemplary MBP sequence is set forth in GenBank Accession No. NP 418458.1.

A "glutathione S-transferase tag" or "GST tag" is derived from an enzyme found in eukaryotes and prokaryotes. A GST tag may be the full length, a portion, or a modified version of the wild-type *E. coli* glutathione S-transferase protein, so long as the presence of the GST tag increases the solubility of the resulting recombinant fusion protein and confers to the fusion protein the binding affinity to glutathione. An exemplary GST sequence is set forth in GenBank Accession No. ACC86120.1 or BAC2126.2.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins*, W. H. Freeman and Co., N.Y. (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, a BRCA2 protein sequence comprised in the fusion protein produced by the method of this invention has at least 80% identity, preferably 85%, 90%, 91%, 92%, 93, 94%, 95%, 96%, 97%, 98%, 99%, or 100% identity, to a reference sequence, e.g., a wild-type human BRCA2 protein), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) J. Mol. Biol. 215: 403-410 and Altschul et al. (1977) Nucleic Acids Res. 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, Proc. Natl. Acad. Sci. USA 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

A "fusion protein consisting essentially of a protein of interest and two (or other specific number) MBP (or GST) tags" is a fusion protein that contains only the protein of interest and two (or other specific number) MBP (or GST) tags, but does not contain any other discernable elements such as full-length proteins, functional domains of proteins, or tags providing any particular binding affinity of antigenicity. This fusion protein, however, may contain one or more amino acid sequences that provide linkage among the protein of interest and the multiple MBP (or GST) tags or provide the correcting reading frame and/or termination of the fusion protein. The linkage between the protein of interest and the MBP (or GST) tags is optionally cleavable by one or more proteases.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter. Other elements that may be present in an expression cassette include those that enhance transcription (e.g., enhancers) and terminate transcription (e.g., terminators), as well as those that confer certain binding affinity or antigenicity to the recombinant protein produced from the expression cassette.

An "antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, Paul (Ed.) *Fundamental Immunology*, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology.

Further modification of antibodies by recombinant technologies is also well known in the art. For instance, chimeric antibodies combine the antigen binding regions (variable regions) of an antibody from one animal with the constant regions of an antibody from another animal. Generally, the antigen binding regions are derived from a non-human animal, while the constant regions are drawn from human antibodies. The presence of the human constant regions reduces the likelihood that the antibody will be rejected as foreign by a human recipient. On the other hand, "humanized" antibodies combine an even smaller portion of the non-human antibody with human components. Generally, a humanized antibody comprises the hypervariable regions, or complementarity determining regions (CDR), of a non-human antibody grafted onto the appropriate framework regions of a human antibody. Antigen binding sites may be wild type or modified by one or more amino acid substitutions, e.g., modified to resemble human immunoglobulin more closely. Both chimeric and humanized antibodies are made using recombinant techniques, which are well-known in the art (see, e.g., Jones et al. (1986) *Nature* 321:522-525).

Thus, the term "antibody," as used herein, also includes antibody fragments either produced by the modification of whole antibodies or antibodies synthesized de novo using recombinant DNA methodologies (e.g., single chain Fv, a chimeric or humanized antibody).

DETAILED DESCRIPTION OF THE INVENTION

I. Introduction

It is well known in the field of recombinant protein production that certain proteins, especially those of relatively large sizes and/or limited solubility, are difficult to produce in satisfactory quantity and quality via conventional methods of recombinant protein expression. The protein encoded by the human breast cancer susceptibility gene 2 (BRCA2) is one example. Yet the BRCA2 protein is of significant importance, because individuals who inherit a mutated allele of the BRCA2 gene experience a high risk of breast, ovarian, and other epithelial cancers. Here the present inventors describe the isolation of the full length recombinant BRCA2 protein from human cells. In one example, the BRCA2 cDNA was cloned into a CMV-driven mammalian expression vector and expressed and purified from human embryonic kidney cells (HEK-293T) using a tandem repeat of the maltose binding protein (MBP) tag located at the N-terminus of the protein for affinity purification. This strategy surprisingly leads to a significant increase in the recombinant production of the protein as well as in the solubility of the protein, therefore achieving higher yield and ease in purification. The expression of this protein from human cells allows for proper post-translational modifications and folding resulting in a protein that can be isolated in quantities unattainable previously.

The purification and isolation of the full length human BRCA2 protein from human cells has not been achieved until now. The advantages of purifying the BRCA2 protein from human cells include: proper post-translational modifications, folding, and substantial increase in yield of biochemically functional protein. Alternative methods of expressing the full length human BRCA2 protein, as for example, in bacteria, yeast, or insect cells result in insolubility, degradation, and yields too low for any practical use.

II. Production of Fusion Proteins with Two or More MBP or GST Tags

A. General Recombinant Technology

Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of a gene of interest, such as a BRCA2 gene, a polynucleotide encoding an MBP or GST tag, and synthetic oligonucleotides can be verified after cloning or subcloning using, e.g., the chain termination method for sequencing double-stranded templates of Wallace et al., *Gene* 16: 21-26 (1981).

A large number of possible tags may be used for practicing the present invention, they include: biotin (small molecule); StrepTag (StrepII) (8 a.a.); SBP (38 a.a.); biotin carboxyl carrier protein or BCCP (100 a.a.); epitope tags such as FLAG (8 a.a.) and myc (22 a.a.); S-tag (Novagen) (15 a.a.); Xpress (Invitrogen) (25 a.a.); eXact (Bio-Rad) (75 a.a.); HA (9 a.a.); VSV-G (11 a.a.); Protein A/G (280 a.a.); HIS (6-10 a.a.); glutathione s-transferase or GST (218 a.a.); maltose binding protein or MBP (396 a.a.); CBP (28 a.a.); CYD (5 a.a.); HPC (12 a.a.); CBD intein-chitin binding domain (51 a.a.); Trx (Invitrogen) (109 a.a.); NorpA (5 a.a.); and NusA (495 a.a.).

B. Coding Sequence for a Protein of Interest

Polynucleotide sequences encoding a target protein, such as a BRCA2 protein, especially a wild-type human BRCA2 protein, are typically known and may be obtained from a commercial supplier.

The rapid progress in the studies of human genome has made possible a cloning approach where a human DNA sequence database can be searched for any gene segment that has a certain percentage of sequence homology to a known nucleotide sequence, such as one encoding a previously identified human BRCA2 protein. Any DNA sequence so identified can be subsequently obtained by chemical synthesis and/or a polymerase chain reaction (PCR) technique such as overlap extension method. For a short sequence, completely de novo synthesis may be sufficient; whereas further isolation of full length coding sequence from a human cDNA or genomic library using a synthetic probe may be necessary to obtain a larger gene.

Alternatively, a nucleic acid sequence encoding a human BRCA2 protein can be isolated from a human cDNA or genomic DNA library using standard cloning techniques such as polymerase chain reaction (PCR), where homology-based primers can often be derived from a known nucleic acid sequence encoding a BRCA2 protein. Most commonly used techniques for this purpose are described in standard texts, e.g., Sambrook and Russell, supra.

cDNA libraries suitable for obtaining a coding sequence for a human BRCA2 protein may be commercially available or can be constructed. The general methods of isolating mRNA, making cDNA by reverse transcription, ligating cDNA into a recombinant vector, transfecting into a recombinant host for propagation, screening, and cloning are well known (see, e.g., Gubler and Hoffman, *Gene,* 25: 263-269 (1983); Ausubel et al., supra). Upon obtaining an amplified segment of nucleotide sequence by PCR, the segment can be further used as a probe to isolate the full length polynucleotide sequence encoding the BRCA2 protein from the cDNA library. A general description of appropriate procedures can be found in Sambrook and Russell, supra.

A similar procedure can be followed to obtain a full-length sequence encoding a human BRCA2 protein from a human genomic library. Human genomic libraries are commercially available or can be constructed according to various art-recognized methods. In general, to construct a genomic library, the DNA is first extracted from a tissue where a BRCA2 protein is likely found. The DNA is then either mechanically sheared or enzymatically digested to yield fragments of about 12-20 kb in length. The fragments are subsequently separated by gradient centrifugation from polynucleotide fragments of undesired sizes and are inserted in bacteriophage λ vectors. These vectors and phages are packaged in vitro. Recombinant phages are analyzed by plaque hybridization as described in Benton and Davis, *Science,* 196: 180-182 (1977). Colony hybridization is carried out as described by Grunstein et al., *Proc. Natl. Acad. Sci. USA,* 72: 3961-3965 (1975).

Based on sequence homology, degenerate oligonucleotides can be designed as primer sets and PCR can be performed under suitable conditions (see, e.g., White et al., *PCR Protocols: Current Methods and Applications,* 1993; Griffin and Griffin, *PCR Technology,* CRC Press Inc. 1994) to amplify a segment of nucleotide sequence from a cDNA or genomic library. Using the amplified segment as a probe, the full-length nucleic acid encoding a BRCA2 protein is obtained.

Upon acquiring a nucleic acid sequence encoding a BRCA2 protein, the coding sequence can be further modified by a number of well known techniques such as restriction endonuclease digestion, PCR, and PCR-related methods to generate coding sequences for BRCA2 proteins, including mutants and variants derived from the wild-type BRCA2 protein. The polynucleotide sequence encoding the desired polypeptide can then be subcloned into a vector, for instance, an expression vector, so that a recombinant polypeptide can be produced from the resulting construct. Further modifications to the coding sequence, e.g., nucleotide substitutions, may be subsequently made to alter the characteristics of the polypeptide.

A variety of mutation-generating protocols are established and described in the art, and can be readily used to modify a polynucleotide sequence encoding a BRCA2 protein. See, e.g., Zhang et al., *Proc. Natl. Acad. Sci. USA,* 94: 4504-4509 (1997); and Stemmer, *Nature,* 370: 389-391 (1994). The procedures can be used separately or in combination to produce variants of a set of nucleic acids, and hence variants of encoded polypeptides. Kits for mutagenesis, library construction, and other diversity-generating methods are commercially available.

Mutational methods of generating diversity include, for example, site-directed mutagenesis (Botstein and Shortle, *Science*, 229: 1193-1201 (1985)), mutagenesis using uracil-containing templates (Kunkel, *Proc. Natl. Acad. Sci. USA*, 82: 488-492 (1985)), oligonucleotide-directed mutagenesis (Zoller and Smith, *Nucl. Acids Res.*, 10: 6487-6500 (1982)), phosphorothioate-modified DNA mutagenesis (Taylor et al., *Nucl. Acids Res.*, 13: 8749-8764 and 8765-8787 (1985)), and mutagenesis using gapped duplex DNA (Kramer et al., *Nucl. Acids Res.*, 12: 9441-9456 (1984)).

Other possible methods for generating mutations include point mismatch repair (Kramer et al., *Cell*, 38: 879-887 (1984)), mutagenesis using repair-deficient host strains (Carter et al., *Nucl. Acids Res.*, 13: 4431-4443 (1985)), deletion mutagenesis (Eghtedarzadeh and Henikoff, *Nucl. Acids Res.*, 14: 5115 (1986)), restriction-selection and restriction-purification (Wells et al., *Phil. Trans. R. Soc. Lond. A*, 317: 415-423 (1986)), mutagenesis by total gene synthesis (Nambiar et al., *Science*, 223: 1299-1301 (1984)), double-strand break repair (Mandecki, *Proc. Natl. Acad. Sci. USA*, 83: 7177-7181 (1986)), mutagenesis by polynucleotide chain termination methods (U.S. Pat. No. 5,965,408), and error-prone PCR (Leung et al., *Biotechniques*, 1: 11-15 (1989)).

C. Modification of Nucleic Acids for Preferred Codon Usage in a Host Organism

The polynucleotide sequence encoding a protein of interest, e.g., BRCA2 protein, can be further altered to coincide with the preferred codon usage of a particular host. For example, the preferred codon usage of one strain of bacterial cells can be used to derive a polynucleotide that encodes a recombinant polypeptide of the invention and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell.

At the completion of modification, the coding sequences are verified by sequencing and are then subcloned into an appropriate expression vector for recombinant production of a protein of interest, such as a BRCA2 protein fused with at least two MBP tags.

III. Expression and Purification of BRCA2 Fusion Protein

Following verification of the coding sequence, a protein of the interest (e.g., a BRCA2 protein) can be produced using routine techniques in the field of recombinant genetics, relying on the polynucleotide sequences encoding the polypeptide disclosed herein.

A. Expression Systems

To obtain high level expression of a nucleic acid encoding a fusion protein of this invention, one typically subclones a polynucleotide encoding the protein of interest and two or more MBP or GST tags in the correct reading frame into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing the polypeptide are available in, e.g., *E. coli*, *Bacillus* sp., *Salmonella*, and *Caulobacter*. Kits for such expression systems are commercially available. Eukaryotic expression systems for mammalian cells (including human cells), yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of the fusion protein of this invention in host cells. A typical expression cassette thus contains a promoter operably linked to the nucleic acid sequence encoding the fusion protein and signals required for efficient polyadenylation of the transcript, ribosome binding sites, and translation termination. The nucleic acid sequence encoding the fusion protein may be linked to a cleavable signal peptide sequence to promote secretion of the polypeptide by the transformed cell. Such signal peptides include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the protein of interest and the MBP or GST tags under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary. Similar to antibiotic resistance selection markers, metabolic selection markers based on known metabolic pathways may also be used as a means for selecting transformed host cells.

When periplasmic expression of a recombinant protein (e.g., a BRCA2-2xMBP or BRCA2-2xGST fusion protein of the present invention) is desired, the expression vector further comprises a sequence encoding a secretion signal, such as the *E. coli* OppA (Periplasmic Oligopeptide Binding Protein) secretion signal or a modified version thereof, which is directly connected to 5' of the coding sequence of the protein to be expressed. This signal sequence directs the recombinant protein produced in cytoplasm through the cell membrane into the periplasmic space. The expression vector may further comprise a coding sequence for signal peptidase 1, which is capable of enzymatically cleaving the signal sequence when the recombinant protein is entering the periplasmic space. More detailed description for periplasmic production of a recombinant protein can be found in, e.g., Gray et al., *Gene* 39: 247-254 (1985), U.S. Pat. Nos. 6,160,089 and 6,436,674.

A person skilled in the art will recognize that various conservative substitutions can be made to any wild-type or mutant/variant protein to produce a fusion protein with two or more MBP or GST tags. Moreover, modifications of a polynucleotide coding sequence may also be made to accommodate preferred codon usage in a particular expression host without altering the resulting amino acid sequence.

B. Transfection Methods

Standard transfection methods are used to produce bacterial, mammalian, yeast, insect, or plant cell lines that express large quantities of a recombinant fusion protein of this invention, which are then purified using standard techniques (see, e.g., Colley et al., *J. Biol. Chem.* 264: 17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132: 349-351 (1977); Clark-Curtiss & Curtiss, *Methods in Enzymology* 101: 347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the fusion protein of this invention.

C. Purification of Recombinantly Produced Fusion Proteins

Once the expression of a recombinant fusion protein with multiple MBP or GST tags in transfected host cells is confirmed, e.g., via an immunoassay such as Western blotting assay, the host cells are then cultured in an appropriate scale for the purpose of purifying the recombinant polypeptide.

1. Purification of Recombinantly Produced Polypeptides from Bacteria

When the fusion proteins of the present invention are produced recombinantly by transformed bacteria in large amounts, typically after promoter induction, although expression can be constitutive, the polypeptides may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 µg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Additional methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing reformation of the immunologically and/or biologically active protein of interest. After solubilization, the protein can be separated from other bacterial proteins by standard separation techniques. For further description of purifying recombinant polypeptides from bacterial inclusion body, see, e.g., Patra et al., *Protein Expression and Purification* 18: 182-190 (2000).

Alternatively, it is possible to purify recombinant polypeptides, e.g., a BRCA2-2xMBP or BRCA2-2xGST fusion protein, from bacterial periplasm. Where the recombinant protein is exported into the periplasm of the bacteria, the periplasmic fraction of the bacteria can be isolated by cold osmotic shock in addition to other methods known to those of skill in the art (see e.g., Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

2. Standard Protein Separation Techniques for Purification

When a recombinant polypeptide of the present invention, e.g., a BRCA2 fusion protein with 2xMBP or 2xGST tags, is expressed in host cells (such as human cells) in a soluble form, its purification can follow the standard protein purification procedure described below. This standard purification procedure is also suitable for purifying BRCA2 fusion proteins obtained from chemical synthesis.

i. Solubility Fractionation

Often as an initial step, and if the protein mixture is complex, an initial salt fractionation can separate many of the unwanted host cell proteins (or proteins derived from the cell culture media) from the recombinant protein of interest, e.g., a BRCA2-2xMBP or BRCA2-2xGST fusion protein of the present invention. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

ii. Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of a protein of interest, e.g., a BRCA2 fusion protein with two or more MBP (or GST) tags. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

iii. Column Chromatography

The proteins of interest (such as a BRCA2 protein fusion of the present invention) can also be separated from other proteins on the basis of their size, net surface charge, hydrophobicity, or affinity for ligands, such as amylose. In addition, antibodies raised against a segment of the protein of interest (e.g., a human BRCA2 protein) can be conjugated to column matrices and the target fusion protein can therefore be immunopurified. All of these methods are well known in the art.

Optionally, a cleavage site recognized by a protease may be designed into the coding sequence of the fusion protein of this invention. For example, a cleavage site can be built in the sequence or sequences linking the target protein (e.g., a human BRCA2 protein) and the MBP or GST tag(s), such that the tag(s) can be readily removed after protease treatment.

It will be apparent to one of skill that chromatographic techniques can be performed at any scale and using equipment from many different manufacturers (e.g., Pharmacia Biotech).

IV. Identification of Inhibitors or Stimulators of BRCA2-RAD51 Protein Interaction Another aspect of the present invention relates to the use of a BRCA2 protein produced according to the method described herein to identify inhibitors of protein interaction between the BRCA2 and RAD51 proteins.

A potentially useful cancer therapeutic would be an inhibitor or stimulator (preferably a small molecule) of BRCA2 and RAD51. A screening method is therefore of great value for identifying inhibitors or stimulators of BRCA2 binding to RAD51, which in turn would inhibit or augment the pathway of homologous recombination, a pathway of repair likely to be engaged by tumor cells to overcome chemotherapy and radiation induced DNA damage. If such a molecule is discovered in this screening process, it can be used directly for cancer therapy, including as an adjuvant to enhance the outcome of standard cancer therapy. The screening method can be performed utilizing several well developed high throughput methods in conjunction with standard combinatorial chemical libraries.

The purified fluorescent RAD51 protein (described previously by the present inventors) is a useful tool in this method. The polarization of fluorescence will decrease upon binding to BRCA2 protein (because of its size and decreased rotational speed). A molecule that blocks the interaction between BRCA2 and RAD51 would result in an increase in polarization of the fluorescent RAD51; conversely, molecules that augment the interaction between BRCA2 and RAD51 would result in a decrease in polarization of the fluorescent RAD51. In this assay, the proteins could be incubated free in solution and analyzed directly in 96- or 384-well format. Alternatively, taking advantage of the 2XMBP tag, one can immobilize the BRCA2 protein on a surface coated with amylose and the binding to fluorescent RAD51 could be measured as an increase in fluorescence after washing out the free unbound RAD51. In this scenario, a decrease or increase in fluorescence would indicate an inhibition or stimulation of fluorescent RAD51 bound to BRCA2, respectively. An alternative means is to use surface plasmon resonance binding assays (e.g., Biacore chips) with either immobilized BRCA2 or RAD51 in conjunction with a chemical library high throughput system analysis.

The advantage of using the full length BRCA2 protein are evident in that previous screens using individual BRC repeats may not recapitulate the full interaction interface for RAD51 binding, as 8 separate BRC repeats are found within the full length protein as well as a carboxy terminal RAD51 binding domain.

EXAMPLES

The following examples are provided by way of illustration only and not by way of limitation. Those of skill in the art will readily recognize a variety of non-critical parameters that could be changed or modified to yield essentially the same or similar results.

Example 1

Purified Human BRCA2 Stimulates RAD51-Mediated Recombination

Introduction

Mutation of the breast cancer susceptibility gene, BRCA2, leads to breast, ovarian, and other epithelial cancers. Mechanistic insight into the functions of BRCA2 has been limited by the difficulty of isolating this large protein (3,418 amino acids). The present inventors report the purification of BRCA2 and show that it loads RAD51, a central component of homologous recombination, onto single-stranded DNA (ssDNA) particularly when contiguous with double-stranded DNA. This loading accelerates displacement of the ssDNA-binding protein, Replication protein-A (RPA), and permits subsequent homologous pairing by RAD51. BRCA2 does not anneal ssDNA complexed with RPA, implying it does not directly function in steps of recombination that involve ssDNA annealing. The inventors' results demonstrate that BRCA2 facilitates assembly of RAD51 onto ssDNA such that recombination can proceed in a rapid and orderly manner. Disruption of this recombinational DNA repair process, which occurs in individuals harboring BRCA2 mutations, leads to chromosomal instability and ultimately, cancer.

Results and Discussion

One of the proposed driving forces behind the tumorigenic process is the onset of genomic instability that, when coupled to repeated rounds of cell division, promotes oncogenesis (1-3). A hallmark of human and mouse cells that are mutant for BRCA2 is severe chromosomal instability marked by an accumulation of chromosomal breaks, translocations, exchanges, and other abnormal structures (4-6). Accordingly, germline mutations in BRCA2 are associated with a highly penetrant incidence of breast and/or ovarian cancer as well as tumors in other tissues and organs (7-9). BRCA2 possesses eight highly conserved repeated sequences positioned within exon 11, termed the BRC repeats, and a carboxy-terminal region that were shown to bind RAD51 (10-13). RAD51 plays a central role in recombination, assembling onto single-stranded DNA (ssDNA) as a nucleoprotein filament, and catalyzing the invasion and exchange of homologous DNA sequences (14-16).

At the cellular level, loss of BRCA2 function results in sensitivity to cross-linking agents, a decrease in homology-directed repair of double-stranded DNA breaks (DSB's), and defects in replication and checkpoint control (4, 17-19). BRCA2 is also required for RAD51-induced focus formation after exposure to DNA damaging agents (20, 21). From studies of domains and homologs (22-28), the inferred role of BRCA2 in mediating RAD51-driven homologous recombination is emerging (29, 30). However, its large size (3,418 amino acids), difficulty in driving high level expression, insufficient solubility, and its propensity to degrade, have precluded isolation of the full length protein which, in turn, has hampered our ability to understand the functions of BRCA2. The present inventors addressed this shortcoming by purifying the full-length human BRCA2 protein from human cells, and defining its biochemical functions with regard to recombinational DNA repair.

Purified Full-Length BRCA2 and its Interactions with Protein.

Figure 1B:
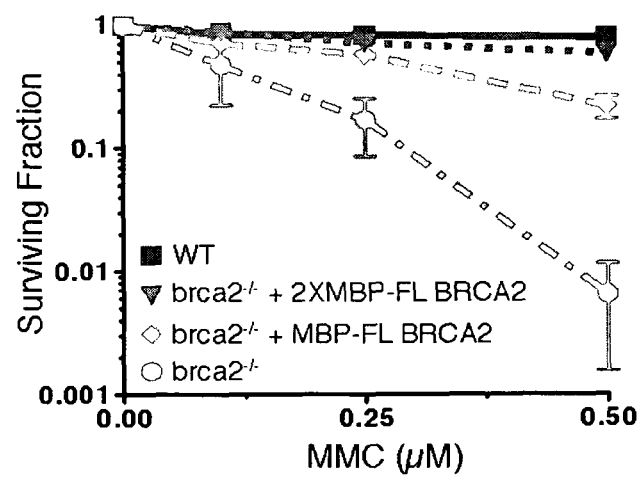
Figure 8A:
FIG. 8. Purification of MBP tagged full length BRCA2. (A) Schematic of strategy used to purify full length human BRCA2 with two tandem repeats of MBP tag at the N-terminus (2XMBP-BRCA2). (B) Western blot (6% SDS-PAGE) using an antibody specific for the carboxy-terminus of BRCA2 showing amylose resin purification of either a single MBP tag fused to the N-terminus of BRCA2 (lanes 1-4) or a double MBP tag at the N-terminus of BRCA2 (lanes 5-8). Lanes 1 & 5: TCL=total cellular lysate. Lanes 2 & 6: B=beads. Remaining BRCA2 bound to amylose beads after maltose elution. Lanes 3 & 7: FT=flow-through (unbound) BRCA2. Lanes 4 & 8: E=eluate. Maltose eluates demonstrate the increased yield of BRCA2 with tandem MBP tag. (C) Amylose resin purification of 2XMBP-BRCA2, followed by NaCl step elutions off the HiTrapQ column. Western blot (6% SDS-PAGE) using the same BRCA2 antibody as in (B). TCL=total cell lysate. Amylose resin eluates (lanes 3-6) were pooled before loading onto the HiTrapQ column.
Figure 8A:
Figure 8A:
Figure 8B:
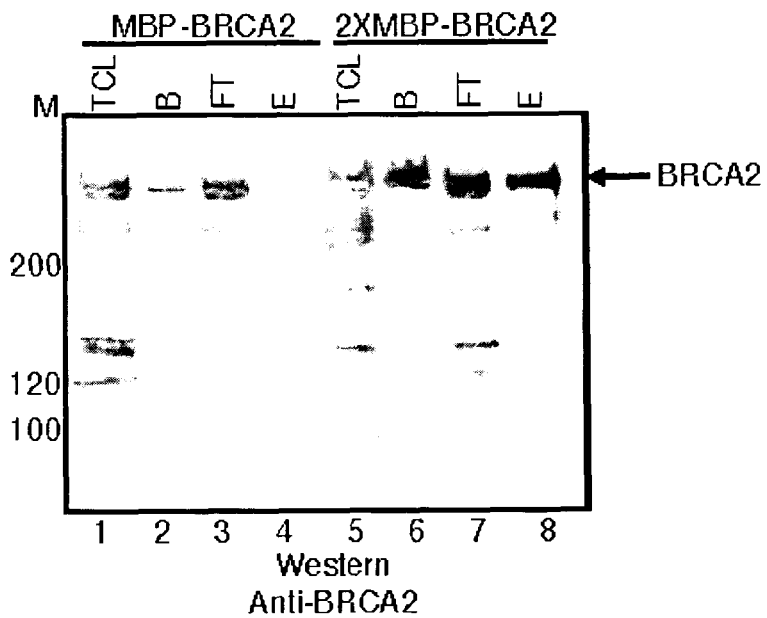
Figure 8C:
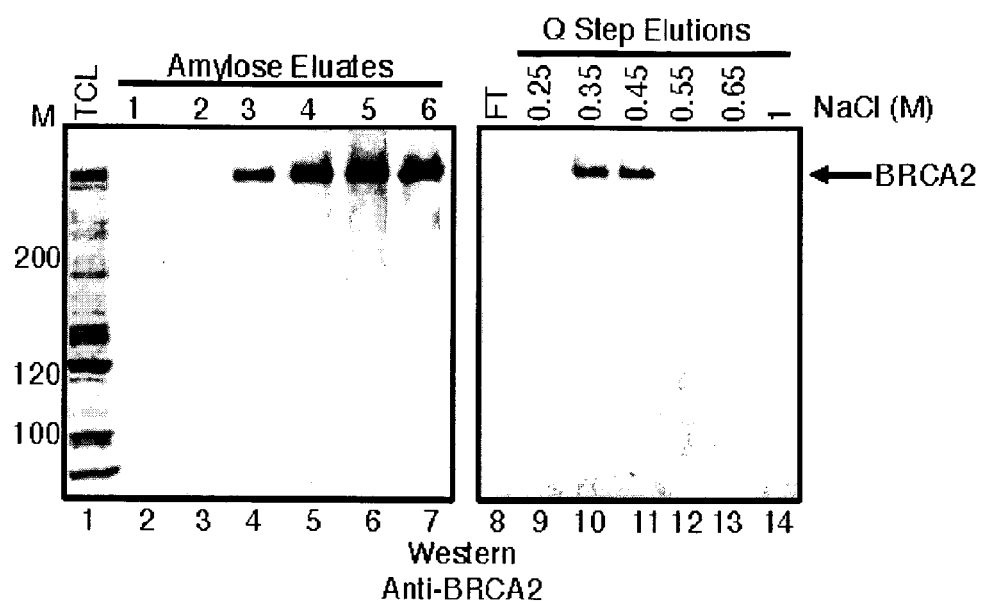
Figure 9A:
FIG. 9. Confirmation of stable MBP-BRCA2 expression in brca2 mutant (VC8) cells by RT-PCR and western blotting. (A) Two sets of primer pairs designed to target and amplify either the MBP tag on the N-terminus of BRCA2 or the C-terminal BRCA2 sequence. (B) Total RNA was isolated from G418-resistant brca2 mutant cells stably transfected with MBP-BRCA2, 2XMBP-BRCA2, or empty vector and utilized in an RT-PCR strategy as depicted in (A) to screen for clones expressing only full length MBP-tagged BRCA2. The ethidium bromide stained gel on the right demonstrates one clone (11) positive for PCR amplification at both ends of the BRCA2 cDNA, while clone (15) is negative. (C) Clones deemed positive by RT-PCR screening were further tested for protein expression by immunoprecipitation of BRCA2 from cellular lysates (using Ab-1), followed by western blotting to detect recombinant BRCA2 expression (using Ab-2). Lane 1 (−) represents the brca2 mutant cells (VC8) transfected with empty vector. Clone 3 (lane 2) was positive for recombinant MBP-BRCA2 expression while clone 4 (lane 3) was negative. Clone 11 (lane 4) was positive for 2XMBP-BRCA2 expression while clone 15 (lane 5) was negative, as expected from the RT-PCR results. Clones 3 (MBP-BRCA2) and 11 (2XMBP-BRCA2) were used in the clonogenic survival assay to assess complementation in FIG. 1B.
Figure 9B:
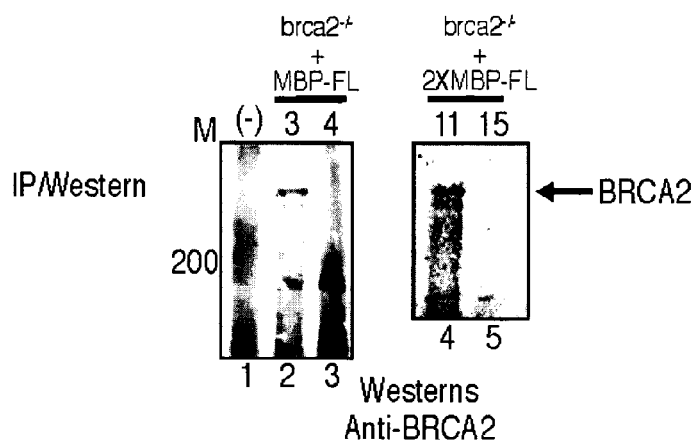
Figure 9C:
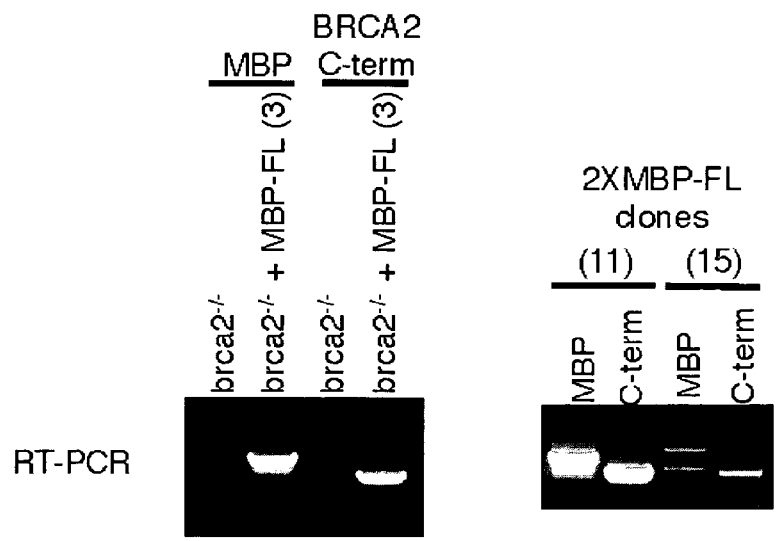

By utilizing a streamlined mammalian expression vector (phCMV1) that is driven by a CMV promoter and by adding two tandem repeats of the Maltose Binding Protein (designated 2XMBP) to tag the N-terminus of human BRCA2 (470 kDa including the two MBP tags), the inventors were able to express significant amounts of protein that could be purified to near homogeneity using a two step purification procedure incorporating an amylose-affinity matrix (FIG. 1A and FIGS. 8A and C). The identity of full length BRCA2 was confirmed by western blotting using antibodies to the C-terminal region of BRCA2 (FIG. 1A, lane 4, and FIGS. 8B and C), as well as by both western blotting using antibodies to the N-terminal MBP tag and mass spectrometric analysis (data not shown). Mass spectrometric analysis of a variable minor band directly below the full length protein confirmed the presence of a truncated BRCA2 species lacking the carboxy terminus. The presence of a third band near the 50 kDa marker (FIG. 1A, asterisk) was confirmed by mass spectrometry to be β-tubulin. The presence of this contaminant appears not to interfere with any of our in vitro studies. The 2XMBP-BRCA2 protein was also expressed in VC8 cells (FIG. 9) and established that it fully complemented brca2 cells in vivo (FIG. 1B); therefore, the tag was not removed for the in vitro studies reported here. Hereinafter, the N-terminal 2XMBP-tagged version of full length BRCA2 is referred to as BRCA2.

Figure 1C:
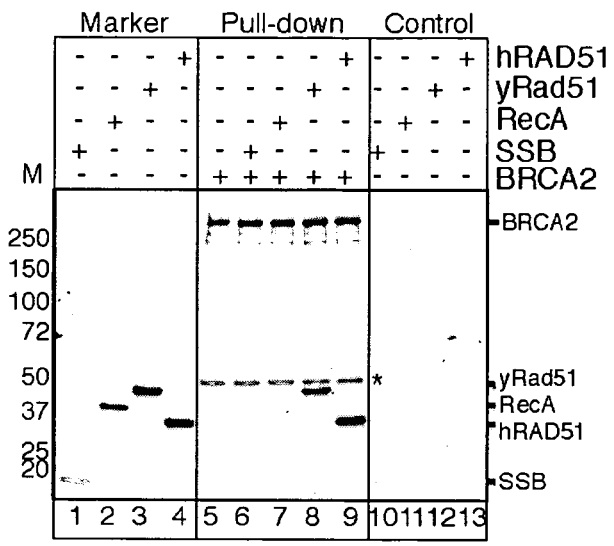
Figure 1D:
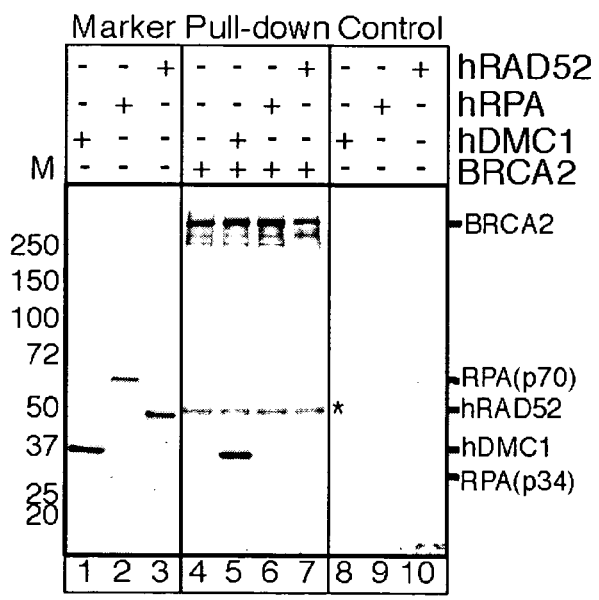

To confirm that the purified BRCA2 was functional in vitro, the inventors first tested its ability to bind recombination proteins that were previously reported to interact. They incubated the BRCA2 with several purified candidate proteins and used the MBP tag to capture the complexes on amylose beads, wash extensively, and finally analyze the complexes on SDS-PAGE gels (FIGS. 1C and D). As expected, human RAD51 bound to BRCA2 (FIG. 1C, lane 9). In agreement with a previous report (31), BRCA2 also bound to DMC1 (FIG. 1D, lane 5), the meiotic counterpart of RAD51. BRCA2 also bound to yeast Rad51 (FIG. 1C, lane 8) but, given the high degree of homology between the two orthologues (~67% identical; 83% homologous (32, 33)), this is not surprising. BRCA2 did not appreciably bind the $E.\ coli$ recombination protein, RecA, (FIG. 1C, lane 7) showing that interaction did not extend to the evolutionary distant bacterial protein. No significant interaction was detected with human RPA (FIG. 1D, lane 6), despite a report in the literature (34), $E.\ coli$ SSB (FIG. 1C, lane 6), or human RAD52 (FIG. 1D, lane 7).

Figure 1E:
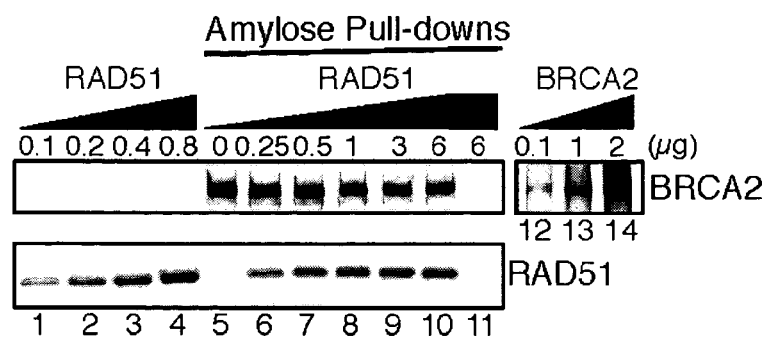
Figure 1F:
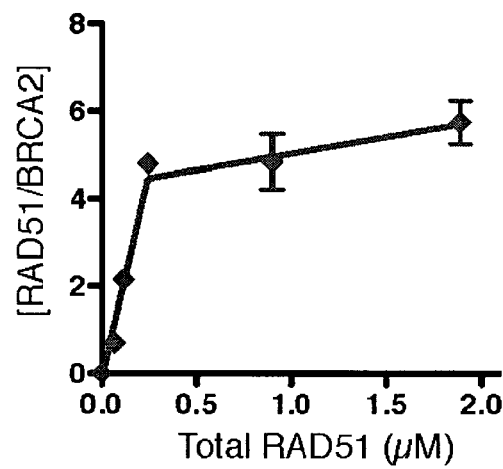

BRCA2 contains eight BRC repeats located within the middle region of the primary sequence of the protein. Various studies have confirmed that many of the BRC repeats can bind RAD51; however, it remains unclear how many binding sites are occupied within the context of the full-length protein. It was next investigated whether BRCA2 and RAD51 form a saturable complex with a defined stoichiometry. Using known concentrations of purified RAD51 (FIG. 1E, lanes 1-4) and recombinant BRCA2 (FIG. 1E, lanes 12-14) as standards, and staining with the sensitive fluorescent protein stain, SyproOrange, the binding of increasing concentrations of RAD51 to a fixed concentration of BRCA2 was quantified; in the absence of BRCA2, RAD51 did not bind non-specifically to the amylose resin (FIG. 1E, lane 11). In the presence of BRCA2 (FIG. 1E, lanes 5-10), the amount of RAD51 bound increased linearly with concentration until about 4.5 (±0.9) RAD51 molecules were bound per BRCA2 (FIG. 1F); afterward, a weaker binding was evident. At the maximum BRCA2 concentration attainable, approximately 6 RAD51 proteins were bound to each BRCA2. The protein complexes formed between BRCA2 and RAD51 were not dependent on magnesium or calcium ions, nucleotide cofactors, or the presence of DNA (data not shown).

Figure 10:
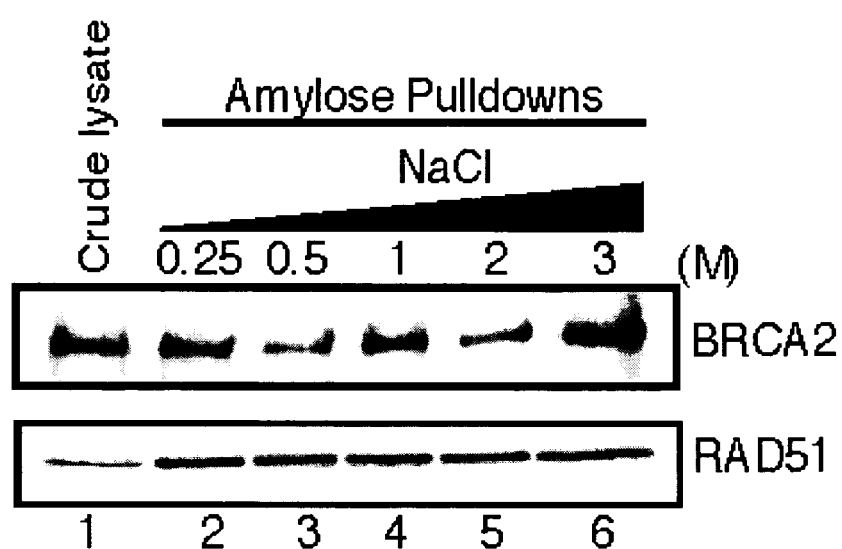
FIG. 10. Endogenous RAD51 bound to 2XMBP-BRCA2 is resistant to high salt washes. 293T cells were transfected with 2XMBP-BRCA2, lysed as described in Materials and Methods in 250 mM NaCl, batch bound to amylose resin, washed extensively with buffer H containing the indicated concentrations of NaCl, and eluted with 10 mM maltose. Half the eluate was then run on a 6% SDS-polyacrylamide gel and probed for BRCA2 (western blot) using a BRCA2 carboxy terminal specific antibody and the other half was run on a 12% SDS-polyacrylamide gel to probe for RAD51 (western blot) using a RAD51 specific antibody.

Because BRCA2 was over-expressed in human 293T cells, it was sought to determine whether recombinant BRCA2 co-purified with endogenous RAD51. It was found that, when eluted from the amylose beads, BRCA2 from cell extracts co-eluted with endogenous RAD51, even when the beads were washed with up to 3 M NaCl (FIG. 10, lanes 2-6). However, the amount of endogenous RAD51 bound to the purified BRCA2 was detectable only by western blotting and was virtually undetectable by Coomassie or SyproOrange staining (FIG. 1A, lane 3, and FIG. 1E, lane 5).

BRCA2 Prefers to Bind ssDNA Over dsDNA.

Figure 2A:
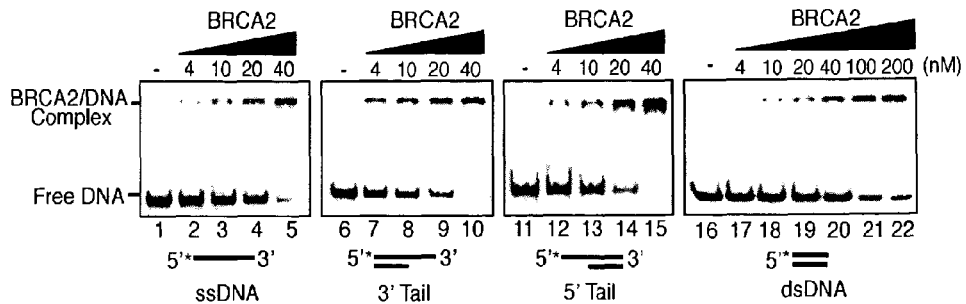
FIG. 2. BRCA2 displays a strong preference for binding tailed and ssDNA substrates over dsDNA. (A) EMSA analyses of BRCA2 binding from left to right: ssDNA, 3' Tail DNA, 5' Tail DNA, and dsDNA. (B) Quantification of the EMSA results in (A). 3' Tail DNA (■), 5' Tail DNA (□) ssDNA (●) and dsDNA (▲). (C) EMSA analyses performed as in (A), except for the presence of 0.5 M or 1 M NaCl. The DNA substrates used were 3' tailed substrate (squares) or ssDNA (circles).
Figure 2B:
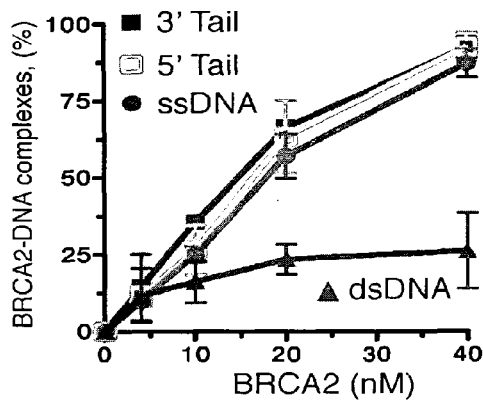
Figure 2C:
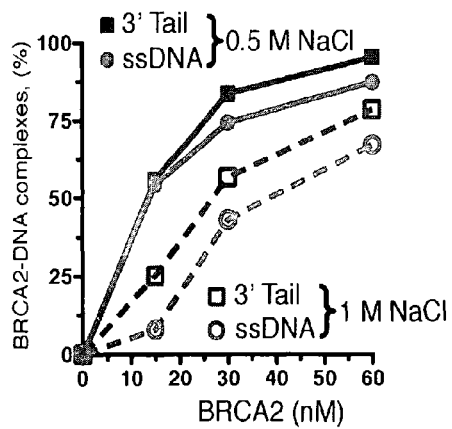

The DNA binding domain of BRCA2 contains both Oligonucleotide-Binding (OB) folds and a tower domain, which engender BRCA2 with potential sites for binding both ssDNA and double-stranded DNA (dsDNA) (23). Indeed, both the carboxy-terminus of BRCA2 and a fusion protein containing BRC repeats 3 and 4 linked to the DNA binding domain of BRCA2 have been shown to bind both ssDNA and dsDNA (22, 23). By using electrophoretic mobility shift assays (EMSA), the ability of BRCA2 was tested to bind ssDNA, dsDNA, and dsDNA with an ssDNA tail (3' tail or 5' tail). BRCA2 bound to all of these substrates; however, those containing ssDNA were strongly preferred over dsDNA (FIGS. 2, A and B). These results are consistent with previous reports on the DNA binding domain of BRCA2 (22). A slight preference for tailed DNA over ssDNA was revealed at higher salt concentrations (FIG. 2C) or in the presence of competitor DNA (data not shown); however, the difference was modest.

BRCA2 Stimulates DNA Strand Exchange by Enforcing Binding of RAD51 to ssDNA.

Figure 11A:
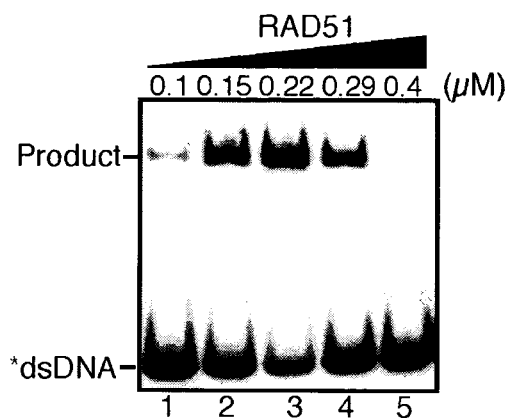
FIG. 11. Optimization of the DNA strand exchange reaction. (A) Autoradiogram of DNA strand exchange reactions utilizing the 3' tailed DNA substrate at different concentrations of RAD51 (lanes 1-5). (B) Autoradiogram showing DNA strand exchange reactions using the 3' tailed DNA substrate in the presence of 0.22 µM RAD51 (lanes 2-7). Standard DNA strand exchange buffer, which contains 2 mM $CaCl_2$, was used. Lane 1: No protein control. Lane 2: ATP omitted. Lane 3: $Mg^{2+}$ omitted. Lanes 4-7: increasing amounts of RPA were incubated with the DNA substrate for 5 minutes at 37° C. prior to the addition of RAD51. (C) Quantification of the data in (A) indicating that optimal exchange occurs at 0.22 µM RAD51. (D) Quantification of the data in (B).

An essential function of RAD51 in recombinational DNA repair is its capacity to homologously pair and exchange DNA strands. To promote this process, RAD51 must assemble onto the 3' ssDNA tails generated by resection of DNA breaks. To mimic the DNA intermediate generated after DSB resection in vivo, the inventors utilized a tailed DNA substrate created by annealing a 42-mer oligonucleotide to a 167-mer to create a 42 base pair (bp) dsDNA region followed by a 125 nucleotide 3' ssDNA overhang (diagramed in FIG. 3A; hereafter termed 3' tailed DNA). To validate the DNA substrate, DNA strand exchange assays was conducted as a function of RAD51 protein concentration using an optimized in vitro DNA strand exchange protocol (FIGS. 11A and C); optimal product formation was at a 1:3 (RAD51:nucleotide) ratio, consistent with the DNA binding stoichiometry reported for RAD51 (16, 35). However, in vivo, filament assembly conditions are not optimal: RAD51 must compete with RPA for binding to the ssDNA (36, 37). Furthermore, RAD51 can bind to both ssDNA and dsDNA; the binding to dsDNA is not productive and, in fact, blocks DNA strand exchange (16, 37). Thus, DNA strand exchange can be stimulated in at least two mechanistically distinct ways.

Figures 3D, 3E:
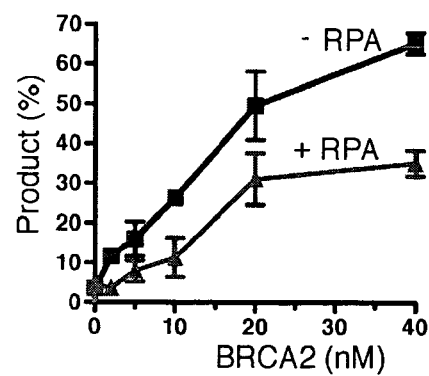
FIG. 3. BRCA2 stimulates DNA strand exchange promoted by RAD51. (A) Diagram of the DNA strand exchange substrates and product. The 3'Tail substrate was the same as described in FIG. 2. (B) Scheme for DNA strand exchange reactions indicating that 3' tailed DNA substrate and radio-labeled dsDNA were pre-mixed before addition of the protein components to start the 30 minute reaction. (C) Autoradiograms of assays performed as described in (B) in the absence (left) or presence (right) of RPA. (D) Quantification of gels in (C) showing effect of BRCA2 in the absence (■) or presence (▲) of RPA. Error bars represent S.D. (E) Scheme for DNA strand exchange reactions in (F) in the absence of RPA. The 3' tailed DNA substrate was incubated first with the indicated BRCA2 and RAD51 for 5 minutes at 37° C., and then the radio-labeled dsDNA was added. (F) Autoradiogram of DNA strand exchange reactions containing excess RAD51 (0.4 µM) in the presence of increasing concentrations of BRCA2. (G) Quantification of the gel in (F).
Figure 12A:
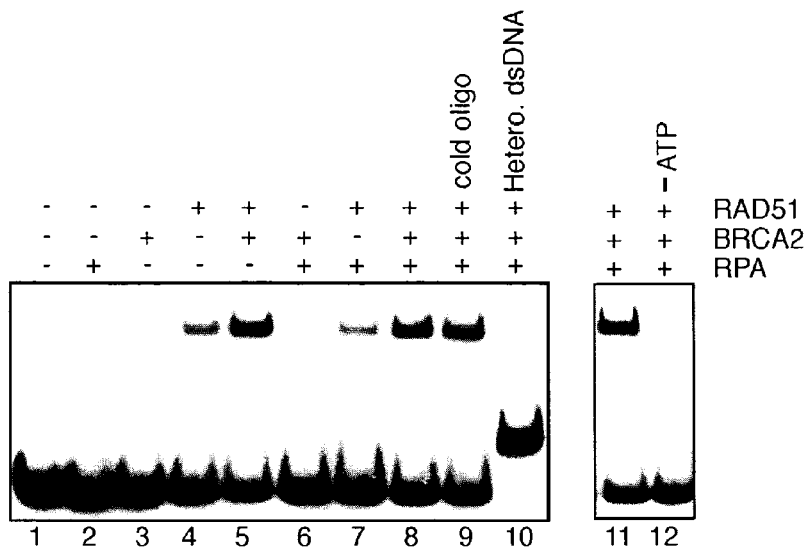
FIG. 12. DNA strand exchange controls. (A) In all DNA strand reactions shown: RPA is 0.1 µM, RAD51 is 0.22 µM, and BRCA2 is 40 nM. Lane 1: no protein control. Lane 2: RPA alone control. Lane 3: BRCA2 alone control. Lane 4: RAD51 alone. Lane 5: BRCA2 and RAD51. Lane 6: RPA and BRCA2. Lane 7: RPA first, RAD51 second. Lane 8: RPA first, BRCA2 and RAD51 second. Lane 9: RPA first, BRCA2 and RAD51 second, with 10-fold excess cold oligonucleotide complementary to the labeled pairing strand in the donor dsDNA present in the deproteinization step. Lane 10: RPA first, BRCA2 and RAD51 second using a heterologous labeled donor dsDNA. Lane 11: RPA first, BRCA2 and RAD51 second. Lane 12: Same reaction as in lane 11 with ATP omitted. (B) Quantification of the data in the autoradiogram (A).
Figure 12B:
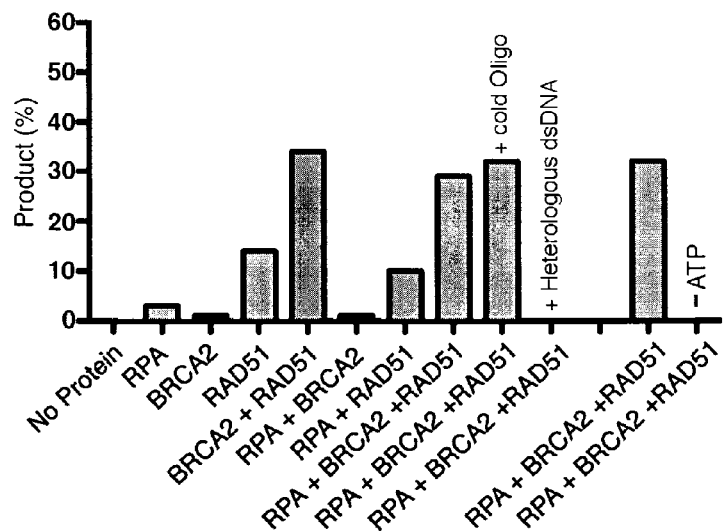
Figure 14:
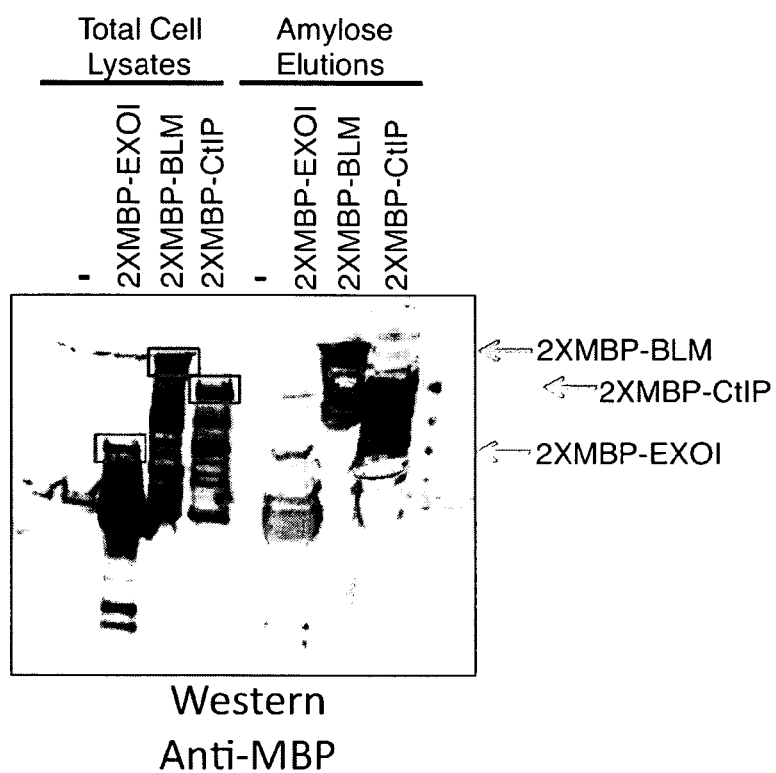
FIG. 14. Western blot analysis of 2xMBP-EXOI, 2xMBP-BLM, and 2xMBP-CtIP. Human 293T cells were transiently transfected with the 2XMBP tagged EXOI, BLM, and CtIP cDNAs in the phCMV1 mammalian expression vector. Cell lysates were harvested 48 hours post transfection and 50 µg of total cell lysate or amylose bound maltose elutions were run on a 4-15% gradient SDS-PAGE gel. The gel was transferred to PVDF membrane and probed with an antibody to MBP (Invitrogen). The boxed bands represent each of the full length proteins with the 2XMBP tag migrating at their respective molecular weights. The amylose purified proteins on the right hand side of the gel are migrating at the same molecular weight but were not boxed. The MBP antibody is not clean and detects multiple nonspecific bands in this Western blot analysis. The amylose purified eluates when run on a coomassie gel appear very clean (not shown here).

Initially, to determine whether BRCA2 affects DNA strand exchange, reactions were performed by using an optimal amount of RAD51 but introducing it simultaneously to a mixture of 3' tailed DNA and dsDNA (FIG. 3B). Indeed, as demonstrated in FIGS. 3C and D, when RAD51 is permitted to assemble on both ssDNA and dsDNA, DNA strand exchange is reduced to background levels (FIG. 3C, lanes 2 & 10). However, if BRCA2 is incubated with RAD51 prior to mixing with the DNA substrates, this inhibition is alleviated in a concentration-dependent manner (FIG. 3C, lanes 3-8; FIG. 3D), suggesting that BRCA2 directs RAD51 to the ssDNA or limits binding to the dsDNA, or both. In the presence of RPA, the stimulation by BRCA2 is maintained, although the magnitude is reduced (FIG. 3C, lanes 11-16; FIG. 3D). This reduction likely stems from the fact that BRCA2-mediated assembly of RAD51 onto the RPA-ssDNA complex is slower than its assembly onto protein-free ssDNA (see FIG. 5 below). At the highest attainable concentration of BRCA2 (40 nM), the stoichiometry of BRCA2:RAD51 approaches 1:6. To confirm that the product did not result from "melting" of the donor duplex DNA and spontaneous annealing during the deproteinization step (38), the inventors performed the same reaction with 10-fold excess of unlabeled oligonucleotide complementary to the labeled pairing strand, and the results were unchanged (FIG. 12A, lane 9). The stimulation was ATP-dependent (FIG. 12A, compare lanes 11 & 12) and did not occur with a heterologous template (FIG. 12A, lane 10); furthermore, BRCA2 alone was ineffective, showing that the low amount of bound endogenous RAD51 was insufficient to promote DNA strand exchange (FIG. 12A, lane 3). These results support a role for BRCA2 in targeting RAD51 to ssDNA, limiting assembly onto the dsDNA partner, or both.

BRCA2 Stimulates DNA Strand Exchange by Preventing Binding of RAD51 to dsDNA.

Figure 3F:
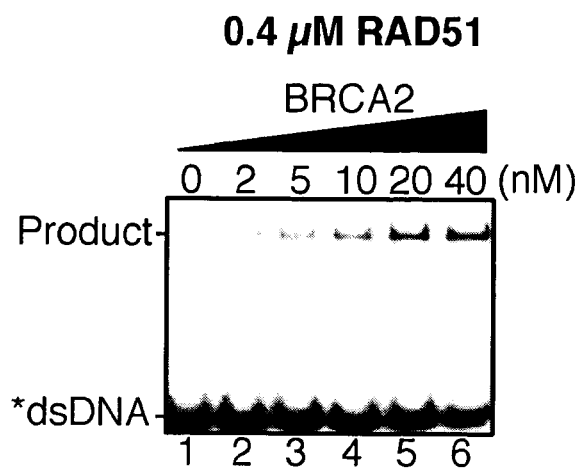
Figure 3G:
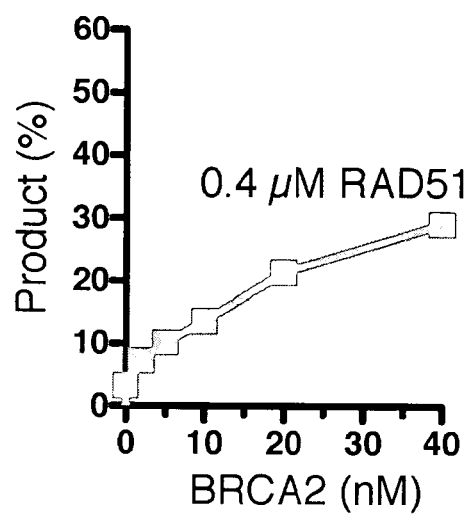
Figure 11B:
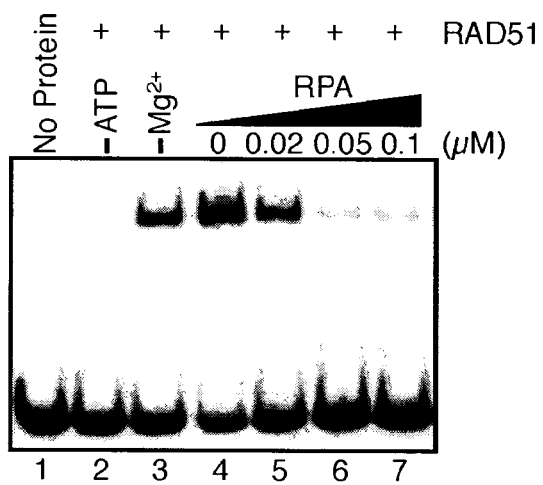
Figure 11C:
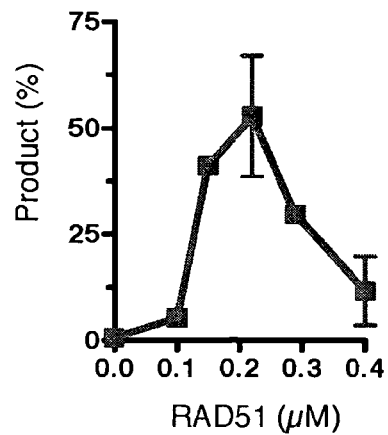
Figure 11D:
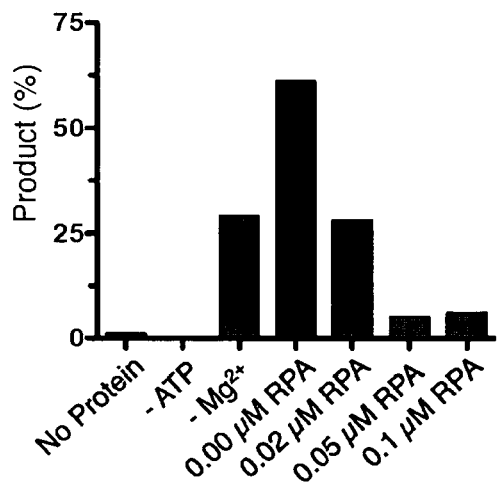

To determine whether BRCA2 slowed or prevented assembly on the dsDNA partner of DNA strand exchange, reactions were performed using a concentration of RAD51 (0.4 µM) sufficient to saturate both the ssDNA and dsDNA present. At such a concentration, DNA strand exchange is inhibited due to binding of the excess RAD51 to the dsDNA target (see FIG. 11A, lane 5; FIG. 11C; and FIG. 3F, lane 1). To optimize filament formation on the ssDNA, BRCA2 and RAD51 are incubated with the 3' tailed ssDNA first, and then the dsDNA is added to initiate the reaction (FIG. 3E); the excess free RAD51 binds the dsDNA partner and inhibit the reaction (FIG. 3F, lane 1). To eliminate complications from competition with RPA, these reactions were done in the absence of RPA. Under these conditions, BRCA2 stimulates DNA strand exchange in a concentration dependent manner (FIGS. 3F, lanes 2-6, and 3G). Taken together with the results of the previous section, these data support the idea that BRCA2 recruits RAD51 to ssDNA, likely by virtue of its affinity for ssDNA, and inhibits assembly of RAD51 onto dsDNA.

BRCA2 Stimulates DNA Strand Exchange Reactions by Overcoming the Inhibition by RPA.

Figure 4A:
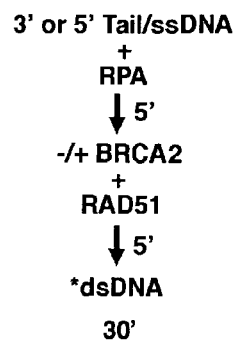
FIG. 4. BRCA2 stimulates RAD51-mediated DNA strand exchange reactions by overcoming the inhibition by RPA. (A) Scheme for the DNA strand exchange reactions used in (B)-(E). The ssDNA-containing substrates were the same as those described in FIG. 2 The DNA substrate was incubated first with RPA for 5 minutes, followed by BRCA2 and RAD51 for 5 minutes, and finally the radio-labeled dsDNA was added to start the 30 minute reaction. The region of homology is located near the 3' (3' tail) or 5' (5' tail) end of the ssDNA. (B) Autoradiograms of assays comparing (left to right): 3' tail, 5' tail, and ssDNA substrates. (C) Quantification of the gels shown in (B): Tailed DNA substrates (squares) versus the ssDNA substrate (circles). (D) Left panel depicts an autoradiogram of assays performed as in (A) utilizing the 3' tail substrate, except *E. coli* RecA (0.22 µM) was substituted for RAD51. The right panel depicts an autoradiogram of reactions performed as in (A) except *E. coli* SSB (0.1 µM) was substituted for RPA. (E) Quantification of assays in (D): *E. coli* RecA (red squares) instead of RAD51 or *E. coli* SSB (blue circles) instead of RPA. The product yield using RecA alone or hRAD51 alone was 59% and 37%, respectively.
Figure 4B:
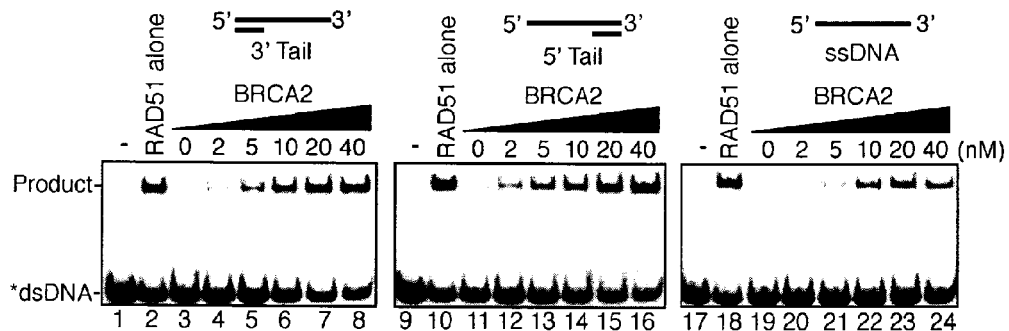

To gain further insight into the mechanism of stimulation provided by BRCA2, the inventors next performed DNA strand exchange assays using an optimal amount of RAD51 but, rather than permitting filament formation on naked ssDNA, the ssDNA was first complexed with RPA (FIG. 4A). RAD51 was subsequently introduced in the presence or absence of BRCA2, and finally, the labeled duplex DNA was added to start the reaction. As expected, incubation of the ssDNA with increasing concentrations of RPA prior to addition of RAD51 severely impaired DNA strand exchange (FIG. 11B, lanes 4-7). As shown in FIGS. 4B and C, increasing amounts of BRCA2 stimulated DNA strand exchange as much as 20-fold, suggesting that BRCA2 accelerates formation of the RAD51 nucleoprotein filament at the presynaptic stage of recombination and alleviates the inhibition posed by RPA. Stimulation by BRCA2 occurred at concentrations as low as 2 nM (FIGS. 4, B and C), and that were sub-stoichiometric relative to the RAD51 concentrations (approximately 100-fold less than RAD51).

Figure 4C:
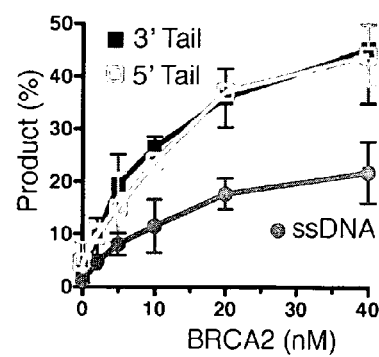
Figure 4D:
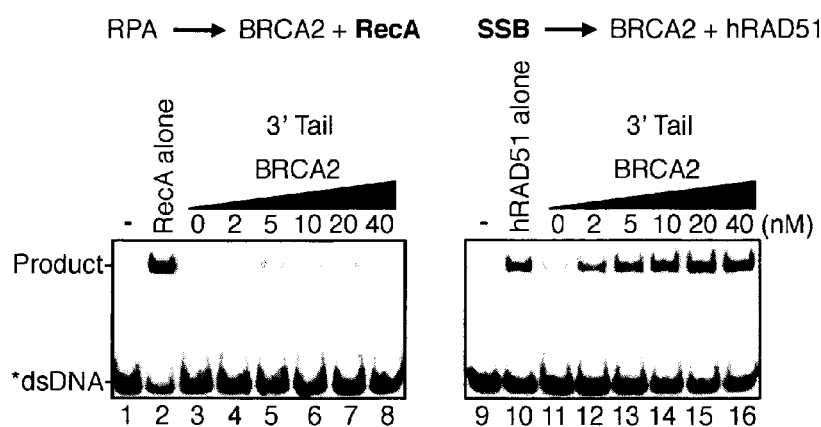
Figure 4E:
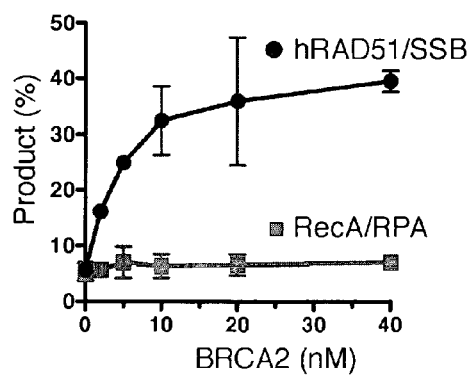

The stimulation of DNA strand exchange by BRCA2 was independent of the nature of the ssDNA tail: 3' versus 5' overhang (FIG. 4B compare lanes 3-8 and 11-16, and 4C). A bias was also not apparent at sub-stoichiometric concentrations of RAD51 (data not shown) where reduced filament occupancy revealed junction specificity for *Ustilago maydis* Brh2 (24). However, the inventors did observe a consistent 2-fold preference for both 3' and 5' tailed DNA substrates over ssDNA, indicating that stimulation by BRCA2 is greater for a DNA substrate containing a junction of ssDNA with dsDNA (FIG. 4C). It is noteworthy that BRCA2 can still stimulate DNA strand exchange using ssDNA without a dsDNA junction, a result similar to that obtained for Brh2 (24). These findings demonstrate that BRCA2 displays two modes of stimulation: one that is targeted to the junction of ssDNA and dsDNA, and a second weaker mode that is independent of the junction. Such behavior is similar to the action of the *E. coli* RecFOR complex (39). Finally, BRCA2 did not stimulate *E. coli* RecA (FIGS. 4D, left panel, and E), a result consistent with the failure of BRCA2 to bind RecA in the pull-down experiments (FIG. 1C). BRCA2 could stimulate RAD51 in the presence of *E. coli* SSB (FIGS. 4D, right panel, and E), implying that neither BRCA2 nor RAD51 need to interact directly with the ssDNA binding proteins, SSB or RPA. This idea is further bolstered by lack of interaction between BRCA2 and either SSB or RPA in the pull-down assays (FIGS. 1C and D). Thus, it appears that direct interactions between BRCA2, RAD51, and DNA are sufficient to stimulate the ability of RAD51 to gain access to the RPA- or SSB-coated ssDNA and to then displace them as the ensuing nucleoprotein filament is formed and extended.

Kinetic Analyses of DNA Strand Exchange Reveal that BRCA2 Stimulates Presynaptic Complex Formation.

To further establish at which point in the recombination process BRCA2 exerts it stimulatory function, a kinetic analysis of DNA strand exchange was performed (FIG. 5). The reaction was performed as depicted in FIG. 5A, allowing RPA to pre-coat the 3' tail DNA substrate followed by the addition of BRCA2 and RAD51. The length of time that BRCA2 was incubated with the RAD51 and the RPA-ssDNA complex was varied either before (FIG. 5A-C) or after (FIG. 13A-C) addition of the radio-labeled homologous dsDNA. BRCA2 imparts a significant stimulation of DNA strand exchange in as little as one minute after incubation with RAD51 and the RPA-ssDNA complex, before the addition of the homologous dsDNA (FIG. 5C). Over time, the differential between the reactions with or without BRCA2 decreases because RAD51 by itself can, albeit slowly, displace the RPA and promote product formation; however, only after 60 minutes does the yield match that seen with BRCA2 at 1 minute (FIG. 5C). A comparison of the linear regions of the time courses shows that presynaptic complex formation on RPA-ssDNA is increased ~20-fold by BRCA2. In contrast, when the time for presynaptic complex formation is held constant, but the time after addition of homologous dsDNA is varied, a steady differential throughout the time course of the reactions is seen (FIG. 13A-C). Thus, these kinetic analyses show that that BRCA2 accelerates the rate of RAD51 nucleoprotein filament formation on ssDNA that is complexed with RPA, confirming the conclusions of the prior section.

BRCA2 Stimulates Presynaptic Complex Formation by Inhibiting ATP Hydrolysis.

Figure 5A:
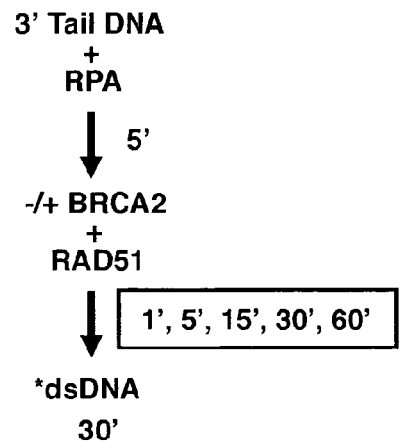
FIG. 5. Kinetic analyses. (A) Scheme for DNA strand exchange reactions indicating that assays were performed as in FIG. 4 except that, after the addition of BRCA2 and RAD51, the proteins were incubated with the 3' tail substrate from 1-60 minutes before addition of the labeled dsDNA to initiate the 30 minute reaction. (B) Autoradiogram of DNA strand exchange assays with 40 nM BRCA2 (+BRCA2) or without (-BRCA2). (C) Quantification of (B); error bars represent the S.D. (D) Inhibition of the ssDNA-dependent ATP hydrolysis activity of RAD51 by BRCA2. The dashed line represents the percentage of DNA-independent ATP hydrolysis by RAD51 (~0.4%; open circle). Error bars represent the S.D. from at least three independent experiments.
Figure 5B:
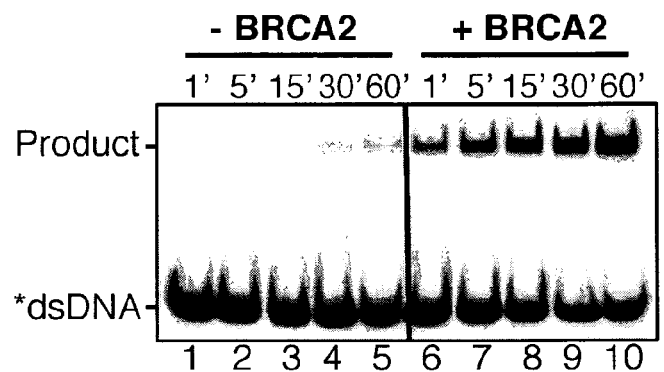
Figure 5C:
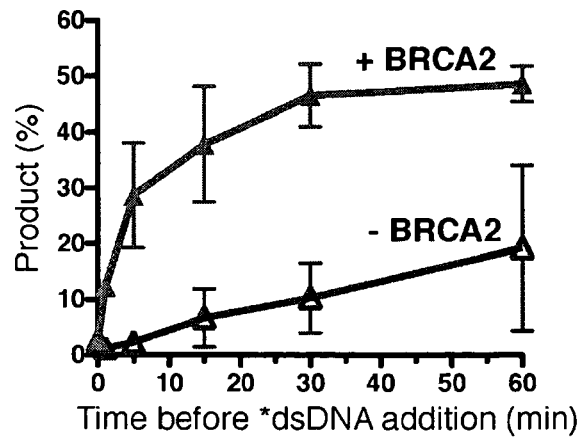
Figure 5D:
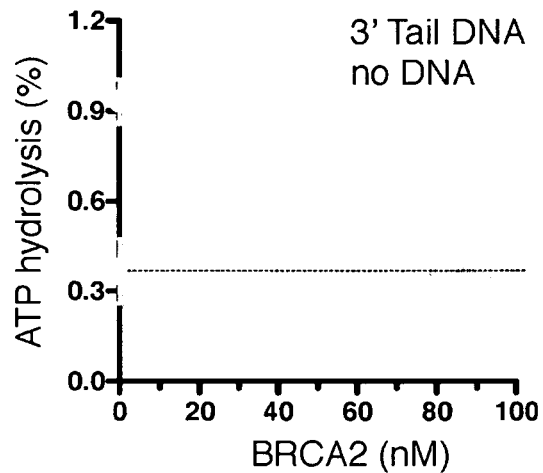

In the inventors' previous work on the BRC-repeat domain of BRCA2, BRC4 and the domain comprising all 8 repeats, $BRC_{1-8}$, were both shown to stabilize ssDNA-RAD51 complexes by blocking the ATPase activity of RAD51 (27). To gain insight into the mechanism by which BRCA2 stimulates presynaptic complex formation, its effect on the ATPase activity of RAD51 was measured. BRCA2 inhibited the ssDNA-dependent ATPase activity of RAD51 in a concentration dependent manner to the level seen in the absence of DNA (FIG. 5D). This inhibition was also observed in the presence of excess DNA, eliminating the possibility that inhibition was due to competition for the same DNA substrate (data not shown). These results suggest the same mechanism for RAD51 nucleoprotein filament stabilization described for the BRC repeats (27); namely, that full length BRCA2 stabilizes the RAD51 bound to the ssDNA substrate by down-regulating its ATPase activity, an activity which is used to inactivate and turnover the RAD51 protein.

BRCA2 does not Anneal ssDNA that is Complexed with RPA.

Figure 6A:
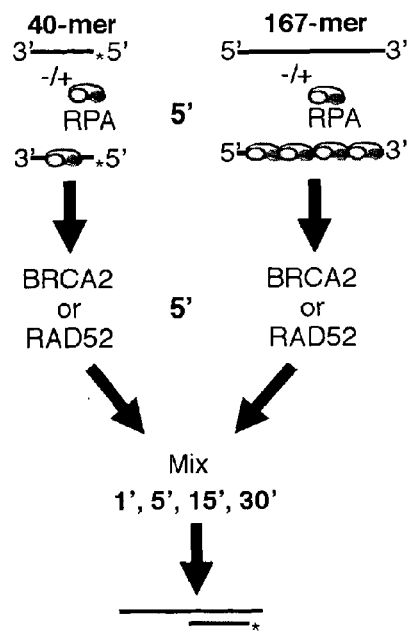
FIG. 6. BRCA2 does not anneal ssDNA that is bound by RPA. (A) Schematic depicting order of addition of components. (B) Autoradiogram of DNA strand annealing assays in the absence of protein (lanes 2-5), BRCA2 alone (lanes 6-9), RAD52 alone (lanes 10-13), RPA alone (lanes 15-18), or RPA first followed by BRCA2 (lanes 19-22), or RPA first followed by RAD52 (lanes 23-26). Lanes 1 and 14 contain the radiolabeled 40-mer alone. (C) Quantification of the autoradiogram in (B). Bars represent: No Protein (grey), BRCA2 (blue), RAD52 (green), RPA (orange), RPA first then BRCA2 (yellow), and RPA first then RAD52 (purple). Error bars show S.D. of three independent experiments.
Figure 6B:
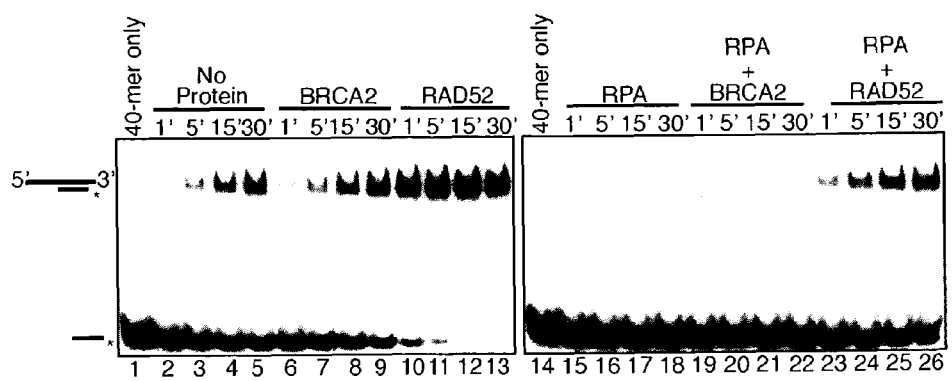
Figure 6C:
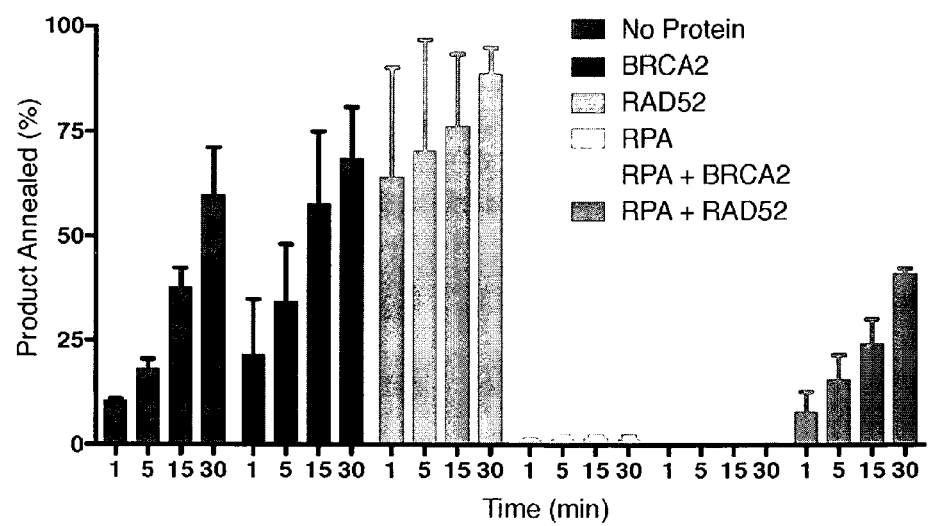

The ability of BRCA2 to accelerate displacement of RPA by RAD51 has some parallels to the RecFOR complex (39, 40) and to yeast Rad52 (yRad52) (41-43), but human RAD52 lacks this ability to stimulate RPA replacement (44). However, because yeast lack a known BRCA2 homologue whereas mammals possess both BRCA2 and RAD52, it is possible that evolutionary changes separated the functions of yRad52 into several mammalian proteins. Another important function of yRad52, and bacterial RecO, is the annealing of complementary ssDNA that is bound by the cognate ssDNA-binding protein (45, 46); consequently, the inventors investigated whether BRCA2 or human RAD52 possess a similar capacity. Complementary ssDNA substrates, with or without saturating human RPA, were incubated with BRCA2 or RAD52 and then mixed (FIG. 6A). FIG. 6B (quantification in FIG. 6C) shows that in the absence of proteins, spontaneous annealing occurred over time (lanes 2-5). BRCA2 marginally increased (lanes 6-9), and RAD52 clearly increased the rate of annealing (lanes 10-13), consistent with a previous report (47). When RPA was added (lanes 15-18), spontaneous annealing was completely blocked. BRCA2 was unable to overcome this inhibition (lanes 19-22), but RAD52 readily annealed the RPA-ssDNA complexes (lanes 23-26). Taken together, these data show that BRCA2 and human RAD52 have assumed divergent roles in mammalian cells. BRCA2 has taken on the functions that stimulate joint molecule formation and DNA strand exchange, whereas RAD52 provides the ssDNA annealing functions of recombination.

These results define the biochemical functions of full length human BRCA2, and they establish that BRCA2 augments the functions of RAD51 that are essential for homologous pairing and DNA strand exchange. Stimulation by BRCA2 is a consequence of several mutually reinforcing effects; it: 1) enforces binding of RAD51 to ssDNA; 2) accelerates the rate of RPA-displacement from ssDNA by RAD51; 3) inhibits the ATPase activity of RAD51; and 4) limits binding to dsDNA. By focusing the assembly of RAD51 onto ssDNA, BRCA2 facilitates the RAD51-mediated displacement of RPA from the ssDNA, which is a key regulatory step of DNA pairing. By enabling formation of the presynaptic complex, BRCA2 permits progression to the subsequent DNA pairing phase of recombinational DNA repair. Furthermore, by inhibiting the ssDNA-dependent ATP hydrolysis of RAD51, BRCA2 preserves the active and most stable form of RAD51, the ATP-RAD51-ssDNA complex (27, 30). Because the rate-limiting step in RAD51 nucleoprotein filament assembly is nucleation of the first several monomers of the filament (48), BRCA2 can act catalytically to stabilize a nucleus by blocking RAD51 self-inactivation and dissociation via its ATPase activity. If the RAD51 molecules bound to BRCA2 do indeed comprise the nucleus, then BRCA2 can stabilize a nascent filament of up to 4-6 RAD51 molecules. In addition, these results show that BRCA2 prevents or slows the assembly of RAD51 onto duplex DNA, an aspect of RAD51 filament assembly that impairs recombination reactions. Based on previous studies with the BRC repeats (27, 28), the inventors believe that interaction with full-length BRCA2 slows nucleation of RAD51 onto dsDNA.

These results also reveal that human BRCA2 stimulates RAD51-mediated DNA strand exchange in a junction-stimulated manner, preferring substrates containing contiguous regions of both single- and double-stranded DNA. In support, the promotion of RAD51 filament formation onto RPA-coated ssDNA was also demonstrated by Liu et al. (this issue) using a different full-length BRCA2 protein expression construct and preparation. Unexpectedly, unlike analogs such as RecFOR and *U. maydis* Brh2, BRCA2 did not demonstrate a defined polarity in loading RAD51 specifically onto the 3' overhanging ssDNA. One possible explanation is that this absence of a bias for pairing 3'-ends reflects the underlying intrinsic behavior of RAD51 (49); in this case, perhaps other proteins may enforce RAD51 filament formation towards the 3' end of the resected DNA. Alternatively, because resection in vivo following a DSB results only in a 3' tailed ssDNA product, there is no need for polarity enforcement in the formation of the RAD51 nucleoprotein filament.

Figure 7:
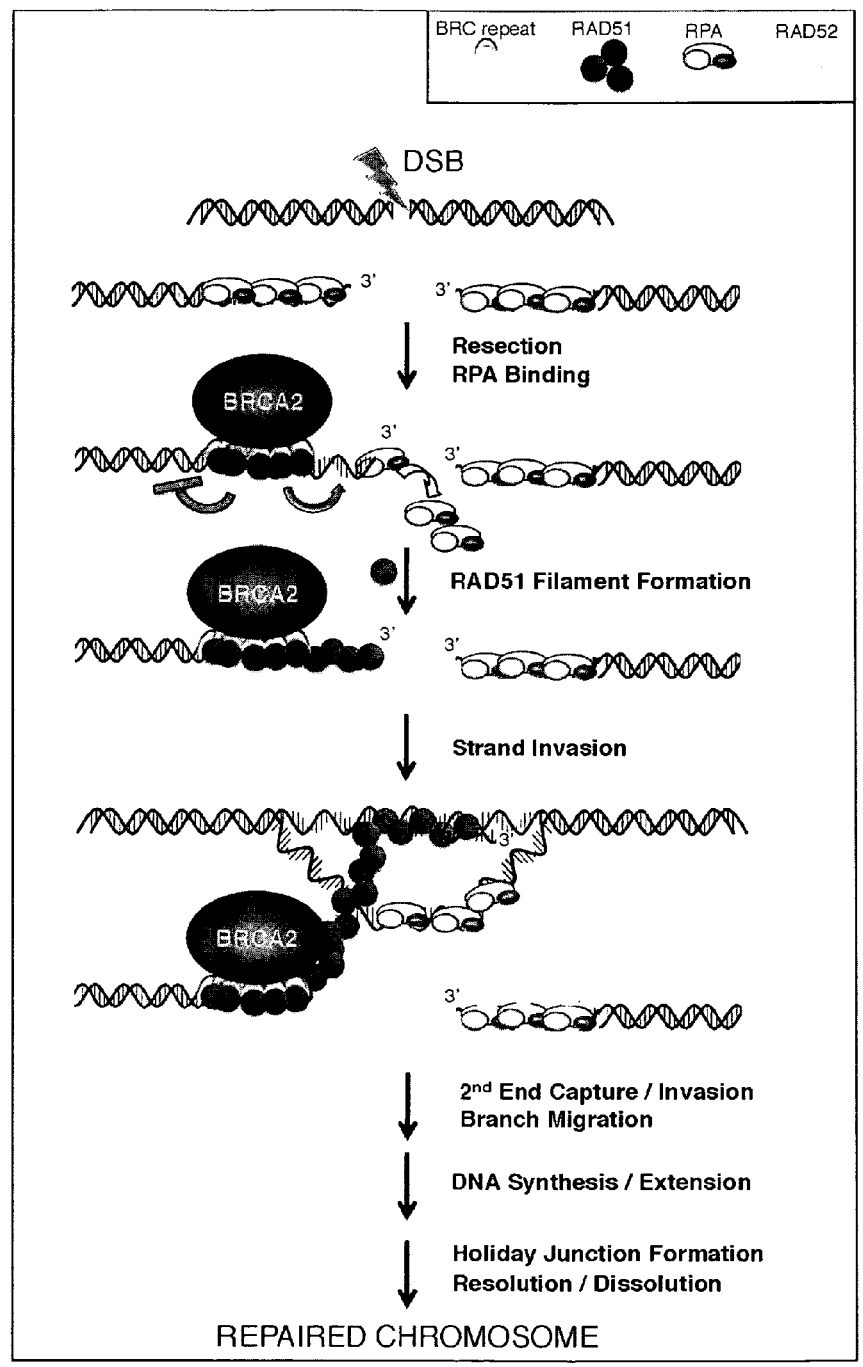
FIG. 7. Model depicting the functions of BRCA2 in recombinational DNA repair. A DSB generated by either exogenous (e.g., ionizing radiation) or endogenous (e.g., metabolic byproducts) sources is resected to reveal 3' ssDNA tails which in vivo are immediately coated by the ssDNA-binding protein, RPA. BRCA2 promotes RAD51 filament formation by loading RAD51 onto the RPA-coated ssDNA tail and also by limiting the assembly of RAD51 onto dsDNA. Because BRCA2 inhibits the ATPase activity of RAD51, the filament on ssDNA is stabilized as the active ATP-bound form of RAD51, allowing subsequent filament extension. The RAD51 nucleoprotein filament finds DNA sequence homology in a donor duplex DNA and promotes DNA strand invasion to form a joint molecule. Completion of DNA DSB repair is then facilitated by multiple proteins acting at several steps, resulting in a repaired chromosome with genetic information intact.

BRCA2 does not possess the capability to anneal the physiological intermediates of recombination, the RPA-ssDNA complexes. This suggests that BRCA2 and RAD52 in mammals have taken on separate functions in recombination (FIG. 7): BRCA2 targets RAD51 to ssDNA to mediate DNA strand invasion into a duplex donor to produce joint molecules, whereas RAD52 anneals RPA-ssDNA complexes in steps or pathways of recombinational repair that could include second-end capture in DSB repair, single-strand annealing, and synthesis-dependent strand annealing. As for many DNA repair pathways, the components involved become more numerous and complex in higher organisms. Human BRCA2 may have evolved to take on a more specialized function while divesting itself of the multiple roles and duties found in a single protein in a simpler organism. Both in vitro and in vivo studies have clarified the role that BRCA2 plays in catalyzing the delivery of RAD51 to sites of DNA damage. The research by the present inventors shows that cells lacking functional BRCA2 would be severely impaired for formation of the intermediate that is essential for recombinational repair: the RAD51 filament assembled on ssDNA. As a consequence, DNA break repair mediated through template-directed repair from homologous sequences within an intact homolog or sister chromosome would be prevented. The loss of this critical repair function in humans harboring BRCA2 mutations would leave only nonhomologous end joining or ssDNA annealing pathways for dsDNA break repair, or alternatively, the broken parts of chromosomes could be lost. The engagement of lower fidelity repair pathways ultimately leads to genome instability and tumor development. In conclusion, the ability to now purify full length human BRCA2, a protein directly responsible for genetically predisposing individuals to substantially high risks for cancer, should open a whole new venue for understanding this very large and complex protein.

Materials and Methods

Expression and Purification of Full Length BRCA2.

The full length cDNA (10.3 kb) of human BRCA2 was cloned into phCMV1 (Genlantis San Diego, Calif.) along with two tandem repeats of the maltose binding protein (MBP) tag located at the N-terminus of BRCA2 using the following strategy: A 2.1 kb PCR fragment containing the N-terminus of BRCA2 was generated using the following primers: RJ-5'KpnINotSTART (5'-TAACCGGTAC-CCAGCGGCCGCCCTATTG GATCCAAAGAGAGG-3') and RJ-3'SacIIEcoRVSbf (5'-TATTGTCCGCGGGATAT CCTGTCCTTCCTGCAGGCATG-3'). A second 1.1 kb fragment was generated from the C-terminus of BRCA2 using the following PCR primers: RJ-5'SacIIAge (5'-TATGGGC CGCGGCAACAAC TACCGGTTTCAGATG-3') and RJ-3'ApaIXhoSTOP (5'-TATTTGG GCCCCTCG AGTTA-GATATATTTTTTAGTTGTAATTG-3'). PCR was done using AccuPrime Pfx DNA polymerase (Invitrogen) set for 25 cycles at an annealing temperature of 60° C. PCR products were then purified using QiaQuick PCR purification kit (Qiagen), digested, gel purified using Qiaexll purification kit (Qiagen) and ligated using T4 DNA Ligase (Invitrogen). The 2.1 kb fragment was digested with KpnI/EcoRV and ligated into pcDNA4/H isMax (Invitrogen) digested with KpnI and EcoRI (blunted). The 1.1 kb fragment was then digested with XhoI and ligated into the previous construct digested with EcoRV and XhoI. Finally, a 7.1 kb internal BRCA2 fragment derived from an SbfI/AgeI digest was ligated into the construct digested with SH/AgeI. MBP was generated by PCR using pMAL (NEB) as a template and the following primers: RJ-5'KPNIMBP (5'-TATTTGGTACCATGAAAATCGAA-GAAGGTAAACTGG-3') and RJ-3'MBPNOTI (5'-TTATTTGCGGCCGCCGGGCCCCTGGAA-CAGAACTTCC-3'). The MBP PCR product was digested with KpnI/NotI and cloned in frame with the N-terminus of BRCA2 by digesting the full length BRCA2 cDNA in pcDNA4 with KpnI/NotI. To generate full length BRCA2 in phCMV1, the multiple cloning site (MCS) of phCMV1 was modified by digesting the vector with BglII/NotI and inserting the following oligonucleotides which were annealed and ligated into the BglII/NotI sites: RJ-5'CMVMCS (5'-GATCTGGTACCAATTCGAGCG CGCTAATAACTG CGGCCGCTTCCGAGCTATCTC-3') and RJ-3'CMVMCS (5'-GGC CATCTCGAGATAG CTCGGAAGCGGCCG-CAGTTATTAGCGCGCTCGAATTGG-3'). The DBD of BRCA2 was then cloned into the NotI/XhoI sites using a PCR product derived from the full length BRCA2 in pcDNA4 using the following primers: RJ-5'BRCA2CTERM_NOTI_6457 (5'-TTATTTGCGGCCGCCCCATATCTCTCTCAA TTTCAACAAGAC-3') and RJ-3'BRCA2CTERMBSTBIXhoI (5'-TTTATTTTC GAACTCGAGTTAGA TATATTTTTAGTTGTAATTGT-GTCCTGC-3'). The BRC repeats 1-8 were then cloned in frame into this construct by digestion with BssHII/NotI of both the vector and the following PCR product using primers: RJ-5'BRC1_2836_BSSHII (5'-TTATTTGCGCGCGAT TTGGTTTATGTTCTTGCAGAGGAG-3') and 3'NOTI-6457 (5'-TTATTTGCGGCCGC AGAAACTTTAATA-GAGTGATTATTTTCT GAAGAACCACC-3'). The fusion at the NotI site generates 3 extra Alanine residues between amino acids 2152 and 2153 of BRCA2. The MBP tagged N-terminus of BRCA2 was PCR amplified from the above pcDNA4 construct using the following primers: RJ-5'KPN-IMBP and RJ-3'BRC1MLUI (5'-TTATTTACGCGTTTTG TTCATGTAATCATTATTTTTTTC TGG-3'). This PCR product was digested with KpnI/MluI and ligated into phCMV1 containing $BRC_{1-8}$ and the DBD by digestion with KpnI/BssHII. This fusion destroyed the MluI/BsshII sites and created a Threonine and Arginine between amino acids 992 and 993 of BRCA2. The second MBP tag was added by generating a PCR product using the following primers RJ-5'MBP2XN (5'-TATTTTGGTACCATGGGCAAAATC-GAAGAA GGTAAACTGG-3') and RJ-3'MBP2XN (5'-TATTTTGGTACCCCCGAGGTTGTT GTTATTGT-TATTG-3') containing KpnI sites on both the 5' and 3' ends. The vector and PCR insert were digested with KpnI and clones containing MBP in the correct orientation were confirmed by sequencing. In order to restore the original BRCA2 sequence, a 7.1 kb SbfI/AgeI fragment was digested out of the original pcDNA4 full length BRCA2 construct and ligated into the phCMV1 construct digested with SbfI/AgeI containing the fusions. All cloning steps were sequence verified (MCLab) and the final construct was verified by utilizing 15 primers spanning 700 bp regions of the full length BRCA2 cDNA. A PreScission Protease (GE Life Sciences) site was engineered in between the second MBP sequence and the start of the BRCA2 ORF such that both MBP tags could be cleaved by incubation with the PreScission Protease enzyme.

In order to express this construct, human 293TD cells (a gift from Rachel Litman, University of Massachusetts Medical School, Worcester, Mass.) were transiently transfected using TurboFect (Fermentas) and cells were harvested 28-36 hours post-transfection. Typically, twenty 15 cm plates containing 70% confluent 293T cells were used for purification. Cells were re-fed with fresh media, DMEM+10% FBS (Invitrogen), before transfection and 16 hours post-transfection. Optimal yields were obtained by harvesting cells 8 hours after the second re-feeding. Cells were harvested in 'buffer H': 50 mM HEPES (pH 7.5), 250 mM NaCl, 5 mM EDTA, and 1 mM DTT with the addition of 1% Igepal CA-630, 3 mM MgCl$_2$, 1 mM ATP, 1 mM PMSF and Protease Inhibitor Cocktail (Roche). The cell suspension was rotated for 20 minutes and then spun down at 10,000 g for 15 minutes in Sorval centrifuge (Oakridge tubes) and the supernatant was incubated overnight with 1 mL of amylose resin (New England Biolabs) per 50 mL of cell lysate, (washed extensively with buffer H before addition to the supernatant). The amylose resin was then spun down at 2,000 g in a swinging bucket rotor (JS 5.3 Beckman), washed one time with lysis buffer, and then poured into a disposable plastic column (Pierce) and washed extensively with buffer H. Up to 3 M NaCl could be used to wash the amylose column with no loss of protein. The protein was then eluted with 10 mM maltose in Buffer 'HG': 50 mM HEPES (pH 7.5), 250 mM NaCl, 0.5 mM EDTA, 10% Glycerol, and 1 mM DTT. These fractions were then pooled and loaded onto a HiTrap Q (GE Life Sciences), washed with buffer HG, and eluted with buffer HG containing 450 mM NaCl (final storage buffer for BRCA2). The full length BRCA2 protein was verified by western blot with antibodies to both the C-terminus of BRCA2 (Ab-2, EMD) and to the N-terminal MBP tag (anti-MBP, Zymed). The concentration of 2XMBP-BRCA2 was determined using an extinction coefficient at 280 nm of 365,160 M$^{-1}$ cm$^{-1}$. The final concentration was adjusted by subtracting out the contributions from the contaminants, β-tubulin and truncated polypeptides, based on SyproOrange quantification. Typical purification yields from twenty 15 cm plates ranged from 50-100 µg. Contaminant bands were cut out as gel slices from Coomassie stained gradient (4-15%) SDS-polyacrylamide gels and analyzed by mass spectrometry (UC Davis Proteomics Core Facility).

Immunodetection of BRCA2.

Cell lysates or purified fractions generated from 293TD cells transfected with 2XMBP-FL BRCA2 were run on 6% SDS-polyacrylamide gels, transferred to PVDF membranes overnight, blocked in 5% milk with 1xTBS-T, and incubated with the primary antibody, Ab-2 (EMD), overnight. For immunoprecipitations (IP's), lysates were quantified for protein content by Bradford method and 1 mg total protein was used in an immunoprecipitation reaction containing 20 µL anti-BRCA2 (Ab-1, EMD) antibody and 40 µL protein G+ agarose (Santa Cruz Biotechnology). IP's were rocked for 2 h at 4° C. and then washed with buffer H followed by resuspension in 15 µL sample buffer. The samples were heated at 55° C. for 4 minutes, loaded onto 6% SDS-polyacrylamide gels, and processed for western blotting as described above. A secondary antibody, anti-mouse or anti-rabbit horse radish peroxidase (hrp) conjugated (Santa Cruz Biotechnology) was incubated on the membranes for 40 minutes. Blots were then washed 4 times and incubated with ECL Plus (Amersham GE healthcare) for 5 minutes before visualization on a Storm PhosphorImager.

Generation of Stable Cell Lines and Clonogenic Survival Assay.

The MBP-BRCA2 and 2XMBP-BRCA2 constructs were stably transfected into VC8 (gift from Malgorzata Zdienicka, Leiden University Medical Center, The Netherlands) BRCA2 mutant hamster cells, using FuGene6 (Roche) transfection followed by selection in HAM's F10 media (Invitrogen) plus 10% FBS (Invitrogen) containing 1 mg/mL G418. To verify expression of BRCA2, total RNA was isolated from VC8 stable cell clones using TRIzol (Invitrogen). 1 µg of total RNA was used in each RT-PCR (Titanium One-step RT-PCR, Clontech) reaction containing either MBP primer set (RJ-5'MBP2XN/RJ-3'MBP2XN) to amplify the MBP tag (1.1 kb) or C-terminal primer set (RJ-5'8269/RJ-3'AGEIBRCA2) to amplify the last 0.9 kb of the BRCA2 open reading frame. RT-PCR reactions were run out on 1% agarose gel and visualized with ethidium bromide staining on an Alpha Innotech UV imager. To confirm expression of MBP-BRCA2 in VC8 cells at the protein level, an immunoprecipitation (IP)/western using Ab-1 (EMD) as the IP antibody and Ab-2 (EMD) as the western antibody was performed. Clones positive for expression were tested for complementation by clonogenic survival response to mitomycin C. Cells were seeded at plating density of 5×10$^5$ cells in 6 cm dishes. Cells were 50-70% confluent at time of drug treatment. Mitomycin C (Sigma) stock was a 1.5 mM stock solution. For treatment of cells, mitomycin C was diluted in 2 mL HAM's F10 media with no serum at the following concentrations: 0.1 µM, 0.25 µM, and 0.5 µM and placed on cells for one hour. After one hour incubation, the media was aspirated off, cells were washed with PBS, then trypsinized and resuspended in 2 mL of HAM's F10+10% FBS. Cells were counted using a hematocytometer, serially diluted, and plated out in triplicate into 6 well plates. Cells were re-fed with media containing penicillin/streptomycin (Hyclone) to prevent any contamination during 8 days of cell growth. After 8 days, the cells were removed from the incubator, washed with 0.9% NaCl (saline solution), and stained with crystal violet. Plates were dried overnight and colonies containing 50 or more cells were counted on each plate and the surviving fraction was determined for each drug treatment.

Protein Affinity Pull-Downs.

Prior to pull-down assays, amylose resin (NEB) was equilibrated with binding buffer 'B': 50 mM HEPES (pH 7.5), 250 mM NaCl, 0.5 mM EDTA, and 1 mM DTT. Purified 2XMBP-BRCA2 (2.4 µg) was incubated with 1 µg purified RAD51, RPA, SSB, RecA, yRad51, DMC1, or RAD52 for 30 minutes at 37° C. and then batch bound to 30 µL of amylose resin for one hour at 4° C. RAD51 and RPA were purified as described previously by Carreira et al., Cell 136, 1032-1043 (2009). SSB, RecA, and yRadS1 were purified as described by Mirshad and Kowalczykowski, Biochemistry 42, 5945-5954 (2003), and Zaitseva et al., J. Biol. Chem. 274, 2907-2915 (1999), respectively. RAD52 was a kind gift from Alex Mazin (Drexel University), and the purification of DMC1 (Amitabh Nimonkar) will be described elsewhere. As controls for non-specific binding to the amylose resin, candidate proteins (1 µg) were incubated with amylose resin in the absence of 2XMBP-BRCA2. The complexes were then washed with buffer B containing 0.1% Igepal CA-630 and resuspended in protein sample buffer, heated at 54° C. for 4 minutes, and loaded onto a 4-15% gradient SDS-polyacrylamide gel (Bio-Rad TGX gel). The gel was run for 1 hour at 100 Volts and stained with SyproOrange (Invitrogen) or Coomassie (Biosafe, Bio-Rad). The protein bands were quantified by ImageQuant software on a Storm 860 PhosphorImager (Molecular Dynamics). The amount of RAD51 pulled down with 2XMBP-BRCA2 in FIG. 1E was determined using standard curves generated from known concentrations of RAD51 and 2XMBP-BRCA2 run in parallel in the same gel. The total input amount of 2XMBP-BRCA2 in each pull-down reaction was 64 nM and the total input amount for RAD51 ranged from 85 nM to 2 µM. The analyses to determine the ratio of RAD51 to 2XMBP-BRCA2 was derived from a fit to a segmented linear regression (GraphPad Prism 5.0b).

For the interactions with endogenous RAD51, 5×10$^6$ 293T cells were transfected with 10 µg of 2XMBP-BRCA2, lysed in Buffer H supplemented with 1% Igepal CA-630 and Protease Inhibitor Cocktail (Roche), batch bound to 40 µL of amylose beads, washed with buffer B, washed with increasing amounts of NaCl in buffer B as indicated, and proteins were eluted with 10 mM Maltose in buffer B. The elutions were then split into half and loaded onto either a 6% or 12% SDS-polyacrylamide gel and a western blot was performed by probing the 12% gel for RAD51 (anti-RAD51, Novus) and 6% gel for 2XMBP-BRCA2 (Ab-2, EMD).

Electrophoretic Mobility Shift Assays.

Oligonucleotide substrates were obtained from either Sigma or IDT (Ultramers) and were purified by polyacrylamide gel electrophoresis (PAGE). The following oligonucleotides were utilized: RJ-167-mer (5'-CTG CTT TAT CAA GAT AAT TTT TCG ACT CAT CAG AAA TAT CCG TTT CCT ATA TTT ATT CCT ATT ATG TTT TAT TCA TTT ACT TAT TCT TTA TGT TCA TTT TTT ATA TCC TTT ACT TTA TTT TCT CTG TTT ATT CAT TTA CTT ATT TTG TAT TA TCC TTA TCT TAT TTA-3'); RJ-5'TAIL-167-mer (5'-ATT TAT TCT ATT CCC TTT ATT TTC TCT GTT TAT TCA TTT ACT TAT TTT GTA TTA ATT TCC TAT ATT TTT TAC T TG T AT T TC T TA T TC A TT T AC T TAT TTT GTA TTA TCC TTA TTT ATA TCC TTT CTG CTT TAT CAA GAT AAT TTT TCG ACT CAT CAG AAA TAT CCG-3'); RJ-PHIX-42-1 (5'-CGG ATA TTT CTG ATG AGT CGA AAA ATT ATC TTG ATA AAG CAG-3'); RJ-Oligo1 (5'-TAA TAC AAA ATA AGT AAA TGA ATA AAC AGA GAA AAT AAA G-3'); RJ-Oligo2 (5'-CTT TAT TTT CTC TGT TTA TTC ATT TAC TTA TTT TGT ATT A-3'). To generate the 3' tailed DNA substrate, RJ-167-mer was radio-labeled with $^{32}$P at the 5'-end and then annealed at a 1:1 molar ratio to RJ-PHIX-42-1. To generate the 5' tailed DNA substrate, RJ-5'TAIL-167-mer was radio-labeled with $^{32}$P at the 5'-end and annealed at 1:1 molar ratio to RJ3'PHIX-42-1. The dsDNA was generated by radio-labeling RJ-Oligo1 with $^{32}$P at the 5'-end and annealing it to RJ-Oligo2. The ssDNA substrate was RJ-167-mer radio-labeled with $^{32}$P at the 5'-end.

2XMBP-BRCA2, at the indicated concentrations, was incubated with 0.2 nM (molecules) radio-labeled DNA substrate for 30 min at 37° C. in DNA strand exchange buffer (25 mM TrisOAc (pH 7.5), 1 mM MgCl$_2$, 2 mM CaCl$_2$, 0.1 µg/µL BSA, 2 mM ATP, and 1 mM DTT). The reactions were resolved by electrophoresis on a 6% polyacrylamide gel in TAE (40 mM Tris-acetate (pH 7.5), 0.5 mM EDTA) buffer for 70 minutes at 60 V. The gel was then dried and exposed to a PhosphorImager screen overnight. The screen was scanned on a Molecular Dynamics Storm 840 PhosphorImager and bands quantified using ImageQuant software. The percentage of protein-DNA complexes was calculated as the free radio-labeled DNA remaining in a given lane relative to the protein-free lane, which defined the value of 0% complex (100% free DNA).

DNA Strand Exchange Assay.

DNA substrates were generated as described above for the EMSA analysis except that RJ-167-mer and RJ-5'TAIL-167-mer were not radio-labeled. The dsDNA donor was generated by first radio-labeling RJ-Oligo1 with $^{32}$P on the 5'-end and annealing it to RJ-Oligo2 at a 1:1 molar ratio. The assay buffer contained: 25 mM TrisOAc (pH 7.5), 1 mM MgCl$_2$, 2 mM CaCl$_2$, 0.1 µg/µL BSA, 2 mM ATP, and 1 mM DTT. All pre-incubations and reactions were at 37° C. The DNA substrates and proteins were at the following concentrations unless otherwise indicated in the figure legend: RPA (0.1 µM); RAD51 (0.22 µM); (3' tail, 5' tail, or ssDNA (4 nM molecules); and dsDNA (4 nM molecules). Unless a time course was shown, the reaction time was 30 minutes. Where proteins were omitted, storage buffer was substituted. RecA (0.22 µM) reactions contained 3 mM ATPyS instead of ATP and were performed in 10 mM MgCl$_2$ in the absence of CaCl$_2$. Reactions utilizing SSB (0.1 µM) contained 5 mM MgCl$_2$. The reaction was terminated with Proteinase K/0.5% SDS for 10 minutes. The reactions were loaded on a 6% polyacrylamide gel in TAE buffer and electrophoresis was at 60 V for 70 minutes. The gel was then dried and exposed to PhosphorImager screen overnight. The percentage of DNA strand exchange product was calculated as labeled product divided by total labeled input DNA in each lane.

ATP Hydrolysis Assay.

The assay was carried out essentially as described, Carreira et al., Cell 136, 1032-1043 (2009). Briefly, BRCA2 at concentrations 0-100 nM was preincubated with 3' tail DNA (0.9 µM nucleotides, nt) in 10 µL of buffer containing 20 mM TrisHCl (pH 7.5), 4 mM MgCl$_2$, 1 mM DTT, 0.5 mM ATP, and 20 µCi/ml [γ$^{32}$P] ATP. The reaction was started by adding RAD51 (0.3 µM) or storage buffer, and further incubated at 37° C. for 90 min. 2 µL aliquots were spotted onto a polyethyleneimine (PEI) thin layer chromatography (TLC) plate (EMD Chemicals) at each time point. The spots were air-dried and the plates were developed in 1 M formic acid and 0.5 M LiCl. The amount of ATP hydrolyzed was determined from dried plates using a Molecular Dynamics Storm 840 PhosphorImager. The percentage of ATP hydrolysis was quantified using ImageQuant software and any residual signal from the BRCA2-only lanes was subtracted from the RAD51+BRCA2 lanes. The results were plotted using GraphPad Prism 5.0b.

Single-Stranded DNA Annealing Assay.

Cold 167-mer (RJ-167 mer, IDT Ultramer, PAGE purified) at 8 nM (molecules) and 5' radio-labeled 40-mer (RJ-Oligo1, Sigma, PAGE purified) at 4 nM (molecules) were each incubated separately in 10 µL reactions containing 25 mM TrisOAc (pH 7.5), 1 mM MgCl$_2$, and 1 mM DTT for 5 minutes with or without RPA (100 nM). The 40-mer is complementary to the 167-mer at the 3' end. All incubations were at 37° C. The oligonucleotides were then incubated with either BRCA2 (40 nM), RAD52 (100 nM), or protein storage buffer for 5 minutes. The two separate reactions were then mixed and incubated for 1, 5, 15, or 30 minutes to allow for annealing. At the indicated time points aliquots were removed and added to stop buffer (4 mg/mL Proteinase K, 1% SDS, and 0.4 µM unlabeled 40-mer (RJ-Oligo2)) complementary to RJ-Oligo1 for 15 minutes. Loading dye was then added to the samples and they were run on 6% polyacrylamide gels in TAE buffer for one hour at 60 V. The gels were dried onto DEAE (Whatman) paper and exposed to a PhosphorImager screen overnight. The screens were scanned on a Storm 860 system (Molecular Dynamics) and bands quantified using ImageQuant. The percentage of annealed product was calculated as the radio-labeled product divided by the total radio-labeled input DNA in each lane.

Example 2

2xMBP-EXOI, 2xMBP-BLM, and 2xMBP-CtIP Fusion Proteins

Additional fusion proteins comprising 2 MBP tags at the N-terminus have been produced in accordance with the same methods described in Example 1. More specifically, the BRCA2 cDNA was excised from the phCMV1-2XMBP vector using a NotI and XhoI restriction enzyme strategy and replaced with a polynucleotide sequence encoding full length human EXOI (exonuclease I, cDNA sequence GenBank Accession No. BC007491.2), BLM (Bloom's syndrome protein, cDNA sequence GenBank Accession No. BC093622.1), or CtIP (retinoblastoma binding protein 8 or RBBP8, cDNA sequence GenBank Accession No. BC030590.1). The resulting fusion polynucleotide sequences were sequenced to confirm in frame translation of the MBP tags with each of the three cDNAs. In all cases, the two MBP tags were placed on the N-terminus of the proteins.

Human EXOI protein is incredibly difficult to detect and express. Fusion with 2XMBP tag has resulted in much higher expression level of recombinant EXOI protein and allowed easier purification: fewer steps are required in the purification process as compared to the process for purifying a recombinant EXOI protein without the tags.

The BLM protein is mutated in Bloom's Syndrome, a rare autosomal recessive disorder. Very little is known about the biological role of human CtIP protein. Their fusion with 2XMBP tag has also produced higher yield in recombinant production of the proteins, as well as allowed easier purification procedures.

In summary, the fusion with 2XMBP provides various benefits such as increased level of recombinant production, higher solubility of the recombinant protein, greater protein stability, and easier purification process. Expression of the 2XMBP recombinant proteins in human 293T cells provides the additional benefit of proper post-translational modification (e.g., glycosylation or phosphorylation), which may be crucial for preserving the natural biological activity/functionality of the proteins.

All patents, patent applications, and other publications, including GenBank Accession Numbers, cited in this application are incorporated by reference in the entirety for all purposes.

REFERENCES

1. C. Lengauer, K. W. Kinzler, B. Vogelstein, Genetic instabilities in human cancers. *Nature* 396, 643-649 (1998).
2. A. S. Kamath-Loeb, L. A. Loeb, E. Johansson, P. M. Burgers, M. Fry, Interactions between the Werner syndrome helicase and DNA polymerase delta specifically facilitate copying of tetraplex and hairpin structures of the d(CGG)n trinucleotide repeat sequence. *J. Biol. Chem.* 276, 16439-16446 (2001).
3. T. D. Tlsty et al., Genomic instability and cancer. *Mutat. Res.* 337, 1-7 (1995).
4. V. P. Yu et al., Gross chromosomal rearrangements and genetic exchange between nonhomologous chromosomes following BRCA2 inactivation. *Genes Dev.* 14, 1400-1406 (2000).
5. L. S. Friedman et al., Thymic lymphomas in mice with a truncating mutation in Brca2. *Cancer Res.* 58, 1338-1343 (1998).
6. G. Donoho et al., Deletion of Brca2 exon 27 causes hypersensitivity to DNA crosslinks, chromosomal instability, and reduced life span in mice. *Genes. Chromosomes Cancer* 36, 317-331 (2003).
7. N. Collins et al., Consistent loss of the wild type allele in breast cancers from a family linked to the BRCA2 gene on chromosome 13q12-13. *Oncogene* 10, 1673-1675 (1995).
8. C. M. Phelan et al., Mutation analysis of the BRCA2 gene in 49 site-specific breast cancer families. *Nat. Genet.* 13, 120-122 (1996).
9. S. V. Tavtigian et al., The complete BRCA2 gene and mutations in chromosome 13q-linked kindreds. *Nat. Genet.* 12, 333-337 (1996).
10. A. K. C. Wong, R. Pero, P. A. Ormonde, S. V. Tavtigian, P. L. Bartel, RAD51 interacts with the evolutionarily conserved BRC motifs in the human breast cancer susceptibility gene brca2. *J. Biol. Chem.* 272, 31941-31944 (1997).
11. P. Bork, N. Blomberg, M. Nilges, Internal repeats in the BRCA2 protein sequence. *Nat. Genet.* 13, 22-23 (1996).
12. G. Bignell, G. Micklem, M. R. Stratton, A. Ashworth, R. Wooster, The BRC repeats are conserved in mammalian BRCA2 proteins. *Hum. Mol. Genet.* 6, 53-58 (1997).
13. F. Esashi et al., CDK-dependent phosphorylation of BRCA2 as a regulatory mechanism for recombinational repair. *Nature* 434, 598-604 (2005).
14. P. R. Bianco, R. B. Tracy, S. C. Kowalczykowski, DNA strand exchange proteins: A biochemical and physical comparison. *Front. Biosci.* 3, D570-D603. (1998).
15. P. Sung, L. Krejci, S. Van Komen, M. G. Sehorn, RadS1 recombinase and recombination mediators. *J. Biol. Chem.* 278, 42729-42732 (2003).
16. P. Baumann, F. E. Benson, S. C. West, Human Rad51 protein promotes ATP-dependent homologous pairing and strand transfer reactions in vitro. *Cell* 87, 757-766 (1996).
17. M. E. Moynahan, A. J. Pierce, M. Jasin, BRCA2 is required for homology-directed repair of chromosomal breaks. *Mol. Cell.* 7, 263-272 (2001).
18. C. F. Chen, P. L. Chen, Q. Zhong, Z. D. Sharp, W. H. Lee, Expression of BRC repeats in breast cancer cells disrupts the BRCA2-Rad51 complex and leads to radiation hypersensitivity and loss of G(2)/M checkpoint control. *J. Biol. Chem.* 274, 32931-32935 (1999).
19. M. Lomonosov, S. Anand, M. Sangrithi, R. Davies, A. R. Venkitaraman, Stabilization of stalled DNA replication forks by the BRCA2 breast cancer susceptibility protein. *Genes Dev.* 17, 3017-3022 (2003).
20. S. S. Yuan et al., BRCA2 is required for ionizing radiation-induced assembly of Rad51 complex in vivo. *Cancer Res.* 59, 3547-3551 (1999).
21. B. C. Godthelp, F. Artwert, H. Joenje, M. Z. Zdzienicka, Impaired DNA damage-induced nuclear Rad51 foci formation uniquely characterizes Fanconi anemia group D1. *Oncogene* 21, 5002-5005 (2002).
22. J. San Filippo et al., Recombination mediator and Rad51 targeting activities of a human BRCA2 polypeptide. *J. Biol. Chem.* 281, 11649-11657 (2006).
23. H. Yang et al., BRCA2 function in DNA binding and recombination from a BRCA2-DSS1-ssDNA structure. *Science* 297, 1837-1848 (2002).
24. H. Yang, Q. Li, J. Fan, W. K. Holloman, N. P. Pavletich, The BRCA2 homologue Brh2 nucleates RAD51 filament formation at a dsDNA-ssDNA junction. *Nature* 433, 653-657 (2005).
25. A. A. Davies et al., Role of BRCA2 in control of the RAD51 recombination and DNA repair protein. *Mol. Cell.* 7, 273-282 (2001).
26. F. Esashi, V. E. Galkin, X. Yu, E. H. Egelman, S. C. West, Stabilization of RAD51 nucleoprotein filaments by the C-terminal region of BRCA2. *Nat Struct Mol Biol* 14, 468-474 (2007).
27. A. Carreira et al., The BRC repeats of BRCA2 modulate the DNA-binding selectivity of RAD51. *Cell* 136, 1032-1043 (2009).
28. M. K. Shivji et al., The BRC repeats of human BRCA2 differentially regulate RAD51 binding on single-versus double-stranded DNA to stimulate strand exchange. *Proc. Natl. Acad. Sci. U.S.A.*, (2009).
29. T. Thorslund, S. C. West, BRCA2: a universal recombinase regulator. *Oncogene* 26, 7720-7730 (2007).
30. A. Carreira, S. C. Kowalczykowski, BRCA2: Shining light on the regulation of DNA-binding selectivity by RAD51. *Cell Cycle* 8, 3445-3447 (2009).
31. T. Thorslund, F. Esashi, S. C. West, Interactions between human BRCA2 protein and the meiosis-specific recombinase DMC1. *EMBO J.* 26, 2915-2922 (2007).

32. A. Shinohara et al., Cloning of human, mouse and fission yeast recombination genes homologous to RAD51 and recA. *Nat. Genet.* 4, 239-243 (1993).
33. Y. Yoshimura, T. Morita, A. Yamamoto, A. Matsushiro, Cloning and sequence of the human RecA-like gene cDNA. *Nucleic Acids Res.* 21, 1665 (1993).
34. J. M. Wong, D. Ionescu, C. J. Ingles, Interaction between BRCA2 and replication protein A is compromised by a cancer-predisposing mutation in BRCA2. *Oncogene* 22, 28-33 (2003).
35. F. E. Benson, A. Stasiak, S. C. West, Purification and characterization of the human Rad51 protein, an analogue of *E. coli* RecA. *EMBO J.* 13, 5764-5771 (1994).
36. T. Sugiyama, E. M. Zaitseva, S. C. Kowalczykowski, A single-stranded DNA-binding protein is needed for efficient presynaptic complex formation by the *Saccharomyces cerevisiae* Rad51 protein. *J. Biol. Chem.* 272, 7940-7945 (1997).
37. S. Sigurdsson, K. Trujillo, B. Song, S. Stratton, P. Sung, Basis for avid homologous DNA strand exchange by human Rad51 and RPA. *J. Biol. Chem.* 276, 8798-8806 (2001).
38. Y. C. Lio, A. V. Mazin, S. C. Kowalczykowski, D. J. Chen, Complex formation by the human Rad51B and Rad51C DNA repair proteins and their activities in vitro. *J. Biol. Chem.* 278, 2469-2478 (2003).
39. N. Handa, K. Morimatsu, S. T. Lovett, S. C. Kowalczykowski, Reconstitution of initial steps of dsDNA break repair by the RecF pathway of *E. coli*. *Genes Dev.* 23, 1234-1245 (2009).
40. K. Morimatsu, S. C. Kowalczykowski, RecFOR proteins load RecA protein onto gapped DNA to accelerate DNA strand exchange: a universal step of recombinational repair. *Mol. Cell.* 11, 1337-1347 (2003).
41. J. H. New, T. Sugiyama, E. Zaitseva, S. C. Kowalczykowski, Rad52 protein stimulates DNA strand exchange by Rad51 and replication protein A. *Nature* 391, 407-410 (1998).
42. A. Shinohara, T. Ogawa, Stimulation by Rad52 of yeast Rad51-mediated recombination. *Nature* 391, 404-407 (1998).
43. P. Sung, Function of yeast Rad52 protein as a mediator between replication protein A and the Rad51 recombinase. *J. Biol. Chem.* 272, 28194-28197 (1997).
44. M. J. McIlwraith et al., Reconstitution of the strand invasion step of double-strand break repair using human rad51 rad52 and RPA proteins. *J. Mol. Biol.* 304, 151-164 (2000).
45. T. Sugiyama, J. H. New, S. C. Kowalczykowski, DNA annealing by RAD52 protein is stimulated by specific interaction with the complex of replication protein A and single-stranded DNA. *Proc. Natl. Acad. Sci. U.S.A.* 95, 6049-6054 (1998).
46. N. Kantake, M. V. Madiraju, T. Sugiyama, S. C. Kowalczykowski, *Escherichia coli* RecO protein anneals ssDNA complexed with its cognate ssDNA-binding protein: A common step in genetic recombination. *Proc. Natl. Acad. Sci. U.S.A.* 99, 15327-15332 (2002).
47. E. Van Dyck, A. Z. Stasiak, A. Stasiak, S. C. West, Visualization of recombination intermediates produced by RAD52-mediated single-strand annealing. *EMBO Rep* 2, 905-909 (2001).
48. J. Hilario, I. Amitani, R. J. Baskin, S. C. Kowalczykowski, Direct imaging of human Rad51 nucleoprotein dynamics on individual DNA molecules. *Proc. Natl. Acad. Sci. U.S.A.* 106, 361-368 (2009).
49. P. Baumann, S. C. West, Heteroduplex formation by human Rad51 protein: effects of DNA end-structure, hRP-A and hRad52. *J. Mol. Biol.* 291, 363-374 (1999).

What is claimed is:

1. A method for recombinantly producing a protein, comprising the steps of:
   (1) introducing an expression cassette into a host cell, wherein the expression cassette comprises a polynucleotide sequence encoding a protein of interest and at least two additional coding sequences, wherein the at least two additional coding sequences encode maltose binding protein (MBP) tags, or wherein the at least two additional coding sequences encode glutathione-S-transferase (GST) tags, such that the expression cassette encodes a fusion protein comprising the protein of interest and at least two MBP or GST tags located at the N-terminus and/or C-terminus of the protein of interest; and
   (2) maintain the cell under conditions permissible for the expression of the fusion protein, whereby producing the fusion protein.

2. The method of claim 1, wherein the fusion protein consists essentially of the protein of interest and two MBP tags or two GST tags.

3. The method of claim 2, wherein the two MBP or GST tags are both located at the N-terminus of the protein of interest.

4. The method of claim 2, wherein one MBP or GST tag is located at the N-terminus of the protein of interest and the other MBP or GST tag is located at the C-terminus of the protein of interest.

5. The method of claim 1, wherein the expression cassette comprises a protease cleavage site between the polynucleotide sequence encoding the protein of interest and the additional coding sequences.

6. The method of claim 1, wherein the protein of interest is a BRCA2 protein, BLM protein, CtIP protein, or EXOI protein.

7. A fusion protein produced from the method of claim 1.

8. The fusion protein of claim 7, wherein the protein of interest is a BRCA2 protein, BLM protein, CtIP protein, or EXOI protein, or a fragment of the protein.

9. The fusion protein of claim 7, wherein the protein of interest is a human BRCA2 protein, BLM protein, CtIP protein, or EXOI protein.

10. The fusion protein of claim 7, which comprises two MBP or GST tags at the N-terminus.

11. An expression cassette comprising at least two polynucleotide sequences, wherein the at least two polynucleotide sequences encode MBP tags, or wherein the at least two polynucleotide sequences encode GST tags.

12. The expression cassette of claim 11, further comprising a CMV promoter.

13. The expression cassette of claim 11, further comprising a polynucleotide sequence encoding a protein of interest.

14. The expression cassette of claim 13, wherein the protein of interest is a BRCA2 protein, BLM protein, CtIP protein, or EXOI protein.

15. A host cell comprising the expression cassette of claim 11.

16. The host cell of claim 15, which is a eukaryotic or prokaryotic cell.

17. A method for recombinantly constructing an expression cassette, comprising the step of ligating a polynucleotide sequence encoding a protein of interest with at least two additional coding sequences, wherein the at least two additional coding sequences encode MBP tags or wherein the at least two additional coding sequences encode GST tags, such that the expression cassette directs the expression of a fusion protein comprising the protein of interest and at least two MBP tags or at least two GST tags located at the N-terminus and/or C-terminus of the protein of interest.

18. The method of claim 17, wherein the protein of interest is a BRCA2 protein, BLM protein, CtIP protein, or EXOI protein.

19. The method of claim 17, wherein the protein of interest is a fragment of a BRCA2 protein, BLM protein, CtIP protein, or EXOI protein.

* * * * *